US006240308B1

(12) United States Patent
Hardy et al.

(10) Patent No.: US 6,240,308 B1
(45) Date of Patent: *May 29, 2001

(54) METHOD AND APPARATUS FOR ARCHIVING AND DISPLAYING ANATOMICO-PHYSIOLOGICAL DATA IN A NORMALIZED WHOLE BRAIN MAPPING AND IMAGING SYSTEM

(75) Inventors: Tyrone L. Hardy, 806 Sagebrush Ct., SE., Albuquerque, NM (US) 87123; Laura D. Brynildson, Albuquerque, NM (US)

(73) Assignees: Tyrone L. Hardy; Medical Instrumentation and Diagnostics Corporation, both of San Diego, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/620,485

(22) Filed: Mar. 22, 1996

Related U.S. Application Data

(63) Continuation of application No. 08/207,234, filed on Mar. 4, 1994, now abandoned, which is a continuation of application No. 07/712,252, filed on Jun. 6, 1991, now abandoned, which is a continuation-in-part of application No. 07/500,788, filed on Mar. 28, 1990, now abandoned, which is a continuation-in-part of application No. 07/290,316, filed on Dec. 23, 1988, now Pat. No. 5,099,846.

(51) Int. Cl.[7] ....................................................... A61B 6/03
(52) U.S. Cl. .......................... 600/407; 600/424; 600/425; 345/420; 345/435; 345/439
(58) Field of Search ..................................... 128/897, 898, 128/653.1, 659; 395/120, 121, 124, 131, 135, 137–139; 364/413.02, 413.13, 413.22, 522; 345/425, 438

(56) References Cited

U.S. PATENT DOCUMENTS

| 3,508,552 | 4/1970 | Hainault | 128/303 |
|---|---|---|---|
| 4,079,450 | 3/1978 | Grimm et al. | 364/200 |
| 4,123,143 | 10/1978 | Yachim et al. | 350/171 |

(List continued on next page.)

FOREIGN PATENT DOCUMENTS

| 2384481 | 11/1978 | (FR) . |
|---|---|---|
| 1074239 | 4/1982 | (SU) . |

OTHER PUBLICATIONS

"Functional Stereotactic Surgery Utilizing CT Data and Computer Generated Stereotactic Atlas" by P.J. Kelly et al., Acta Neurochirurgica, Suppl. 33, pp. 577–583 (1984).

"Cerebral Cortical Localization: Application and Validation of the Proportional Grid System in MR Imaging," by Helmuth Steinmetz et al., Journal of Computer Assisted Tomography, vol. 13, No. 1, pp. 10–19 (1989).

(List continued on next page.)

*Primary Examiner*—David M. Shay
(74) *Attorney, Agent, or Firm*—Jeffrey D. Myers; Donovan F. Duggan; Deborah A. Peacock

(57) ABSTRACT

Method and apparatus for archiving and simultaneous display of brain scan images and a plurality of brain maps. The brain maps are proportioned to the individual brain of the scan images by a three-dimensional alignment process. Two-dimensional and three-dimensional displays are supported.

37 Claims, 24 Drawing Sheets

U.S. PATENT DOCUMENTS

| | | | |
|---|---|---|---|
| 4,223,227 | 9/1980 | Horwitz | 250/491 |
| 4,230,117 | 10/1980 | Anichkov | 128/303 |
| 4,259,725 | 3/1981 | Andrews et al. | 364/521 |
| 4,278,888 | 7/1981 | Wagner | 250/445 T |
| 4,341,220 | 7/1982 | Perry | 128/630 |
| 4,350,159 | 9/1982 | Gouda | 128/303 B |
| 4,386,602 | 6/1983 | Sheldon et al. | 128/4 |
| 4,463,758 | 8/1984 | Patil et al. | 128/303 B |
| 4,502,147 | 2/1985 | Michaels | 378/206 |
| 4,583,538 | 4/1986 | Onik et al. | 128/303 |
| 4,597,380 | 7/1986 | Raif et al. | 128/6 |
| 4,598,368 * | 7/1986 | Umemura | 364/413.13 |
| 4,608,635 | 8/1986 | Osterholm | 364/414 |
| 4,608,977 | 9/1986 | Brown | 128/303 |
| 4,617,925 | 10/1986 | Laitinen | 128/303 B |
| 4,638,798 | 1/1987 | Shelden et al. | 128/303 B |
| 4,651,732 | 3/1987 | Frederick | 128/303 R |
| 4,653,112 | 3/1987 | Ouimette | 382/69 |
| 4,685,070 * | 8/1987 | Flinchbaugh | 364/522 |
| 4,702,571 | 10/1987 | Barber | 350/516 |
| 4,706,665 | 11/1987 | Gouda . | |
| 4,729,098 | 3/1988 | Cline et al. | 361/414 |
| 4,777,598 | 10/1988 | Kellar et al. | 364/413.22 |
| 4,790,026 | 12/1988 | Gennery et al. | 382/49 |
| 4,791,934 | 12/1988 | Brunnett | 128/653 |
| 4,813,588 | 3/1989 | Srivastava et al. | 228/103 |
| 4,832,049 | 5/1989 | Matsushita et al. | 128/781 |
| 4,835,712 * | 5/1989 | Drebin et al. | 395/124 |
| 4,856,528 | 8/1989 | Yang et al. | 128/653 |
| 4,879,668 * | 11/1989 | Cline et al. | 395/130 |
| 4,884,566 | 12/1989 | Mountz et al. | 128/303 B |
| 4,888,713 | 12/1989 | Falk | 364/522 |
| 4,905,702 | 3/1990 | Foss | 128/665 |
| 4,919,516 | 4/1990 | Petran et al. | 350/171 |
| 4,977,505 | 12/1990 | Pelizzari | 364/413.19 |
| 5,099,846 | 3/1992 | Hardy | 128/653.1 |

OTHER PUBLICATIONS

"A Method for MRI and CT Mapping of Diencephalic Somatotopography," by T.L. Hardy, Proceedings of the Microelectrode Meeting, France, Sep. 1987, Stereotactic and Functional Neurosurgery, Reprint, vol. 52, pp. 242–249 (1989).

Textbook *Co–Planar Stereotaxic Atlas of the Human Brain*, by J. Talairach, et al., Theieme Medical Publishers, New York 1988.

Textbook, *Introduction to Stereotaxis with an Atlas of the Human Brain* by Schaltenbrand & Bailey, 1959.

Textbook, *Variations and Connections of the Human Thalamus* by Van Buran & Borke, 1972.

"Stereotactic CT Atlasas" by T. Hardy, Chapter 34 L.D. Lunsford, ed., *Modern Stereotactic Surgery*) 1988.

Textbook, *Atlas for Stereotaxy of the Human Brain*, Schaltenbrand et al 2nd ed. Stuttgard, Thieme (1977) (copy provided).

Textbook, *Radiologic Anatomy of the Brain*, Salamon et al Springer–Verlag (1976).

Textbook, *Stereotaxy of the Human Brain: Anatomical, Physiological and Clinical Applications*, 2nd Rev. Ed. Thieme (1982) (selected pages attached).

Textbook, *Vergleichende Lokalisationslehre der Grosshirnrinde*, K. Boardman Barth (1909).

The Magnetic and Electric Fields Agree with Intracranial Localizations of Somatosensory Cortez, Sutherling, et al *Neurology* 38 1705 (1988.

"Computerized Optimization of $^{125}$I Implants in Brain Tumors" by B. Bauer–Kirpes, Ph.D. *J. Radiation Oncology Biol. Phys.*, vol. 14, pp. 1013–1023 (1987).

"External Stereotactic Irradiation by Linear Accelerator" by F. Columbo, M.D., et al. *Neurosurgery*, vol. 16, No. 2; pp. 154–159 (1985).

Advertisement: "Elekta" Leksell Micro–Stereotactic System (1989).

"The University of Florida Radiosurgery System" by W.A. Friedman, M.D. 1989, Elsevier Science Publishing Company, Inc.

"CASS: A Program for Computer–Assisted Stereotaxic Surgery," Proceedings of the 5th Annual Symposium on Computer Application in Medical Care, T.L. Hardy and J. Koch; Washington, D.C., 1981, pp. 1116–1126.

"Computer–Assisted Stereotaxic Surgery," Hardy, T.L. and Koch, J.; *Appl. Neurophysiol.*, vol. 45, pp. 396–398 (1982).

"Computer Graphics with Computerized Tomography for Functional Neurosurgery," Hardy, T.L., Koch, J., and Lassiter, A., *Appl. Neurophysiol.*, vol. 46, pp. 217–226 (1983).

"A Portable Computerized Tomographic Method for Tumor Biopsy," Hardy, T.L., Lassiter, A., and Koch, J., *Acta. Neurochir.* [Suppl.], (Wien) p. 444 (1983).

"Computer–Assisted Stereotactic Laser Microsurgery for the Treatment of Intracranial Neoplasms" by P. Kelly et al. *Neurosurgery*, vol. 10, No. 3, pp. 324–331 (1982).

"Computer Simulation for the Stereotactic Placement of Interstitial Radionuclide Sources onto CT–Defined Tumor Volumes," Kelly et al., *Neurosurgery*, pp. 412–444 (1984).

"Stereotactic Surgical System Controlled by Computed Tomography" by M. Koslow, M.D., et al. *Neurosurgery*, vol. 8, pp. 72–82 (1981).

"The Ill–Conditioning in Stereotaxic Irradiation: Optimization of Isodoses Arrays Distribution Using the Singular Values Decomposition," Conference Eighth International Conference, Jun. 8–10, 1988.

"Exploring Design Space: Optimization as Synthesizer of Design and Analysis" by A.R. Parkinson et al. *Computers in Mechanical Engineering*, Mar. 1985, pp. 28–36.

"The Role of Computed Tomography and Digital Radiographic Techniques in Stereotactic Procedures for Electrode Implantation and Mapping, and Lesion Localization," by T.M. Peters et al., *Appl. Neurophsyiol.*, vol. 46, pp. 200–205 (1983).

"Measurements of Dose Distributions in Small Beams of 6MV X–Rays" by R.K. Rice et al. *Phys. Med. Biol.*, vol. 32, No. 9 (1987), pp. 1087–1099.

"Development of a Computerized Microstereotaxis Method for Localization and Removal of Minute CNS Lesions Under Direct 3–D Vision" by C.H. Sheldon et al. *Journal of Neurosurgery*, Technical Report, vol. 52, pp. 21–27 (1980).

Sales Brochure of Stereotactic Medical Systems, Inc., designed by Patrick Kelly et al.

"A System for Anatomical and Functional Mapping of the Human Thalamus" by C.J. Thompson et al. *Computers and Biomedical Research* (1977), pp. 9–24.

"A CT–Based Computerized Treatment Planning System for I–125 Stereotactic Brain Implants" by K. Weaver, Ph.D., et al. *J. Radiation Oncology Biol. Phys.*, vol. 18, pp. 445–454 (1989).

"Linear Accelerator as a Neurosurgical Tool for Stereotactic Radiosurgery" by K.R. Winston, M.D., et al. *Neurosurgery*, vol. 22, No. 3 (1988), pp. 454–462.

Dictionary definition of "isodose".

"A System for Anatomical and Functional Mapping of the Human Thalamus," Thompson, C.J., Hardy, T.L., and Bertrand, G., *Comput. Biomed. Res.*, vol. 19, pp. 9–24 (1977)—textbook.

* cited by examiner

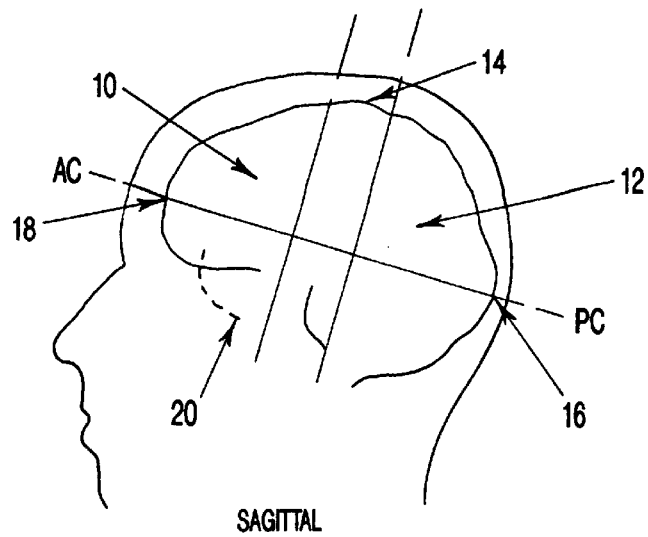
SAGITTAL
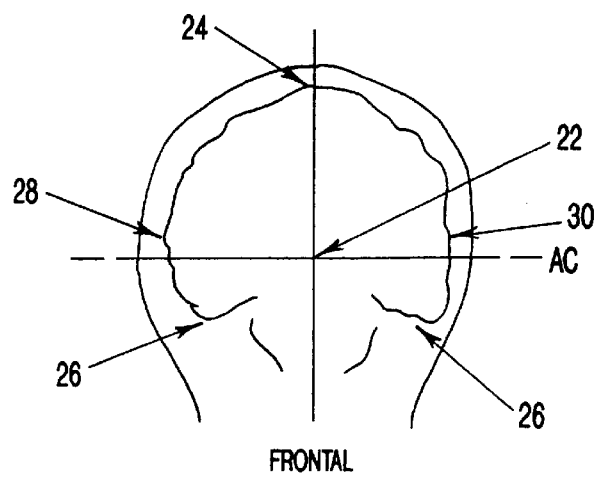
FRONTAL
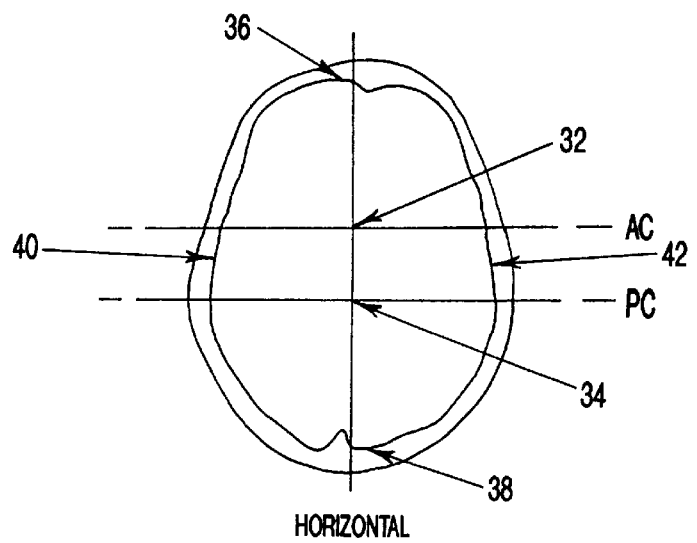
HORIZONTAL
FIG-6

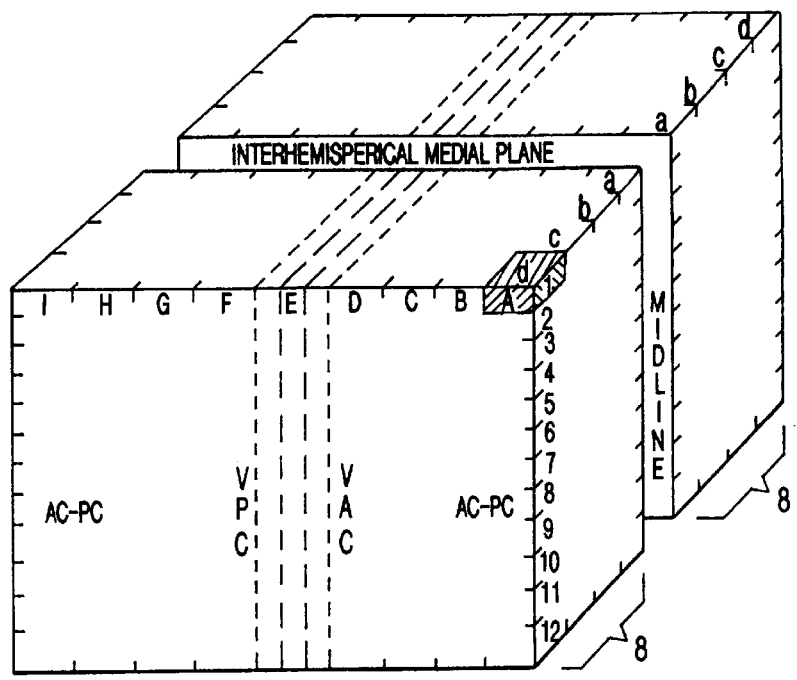
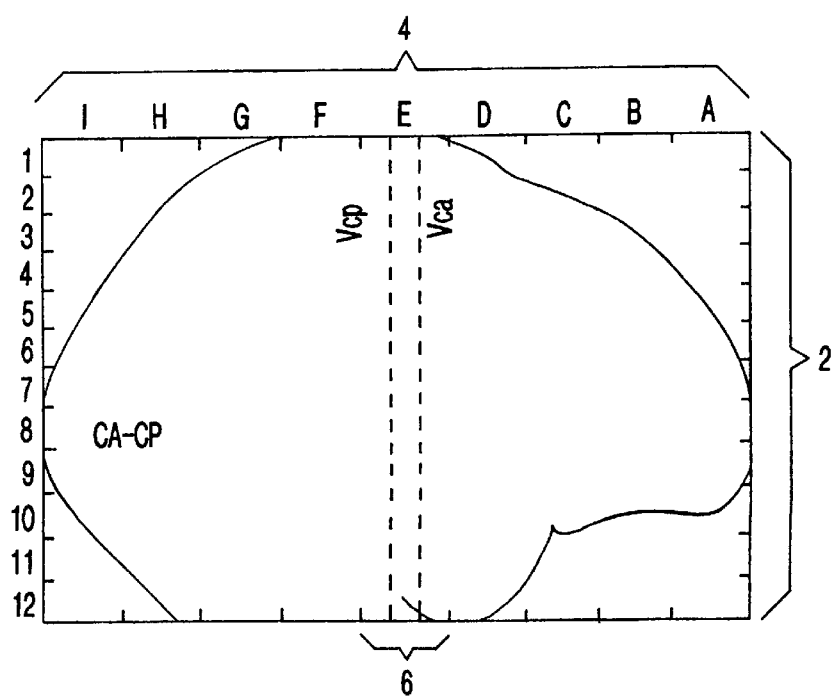
FIG-18

COMPUTER CODING OF SIMULATION RESPONSES

| | | | |
|---|---|---|---|
| MOTOR | TONGUE | 1 | RELIABILITY |
| | FACE | 2 | |
| | NECK | 3 | 3 GOOD 1 VOLT OR LESS |
| | THUMB | 4 | 2 FAIR 1.1 – 1.9 VOLTS |
| | FINGERS | 5 | 1 POOR 2 VOLTS AND OVER |
| | HAND | 6 | |
| | ARM | 7 | NOTE: EACH VOLT |
| | LEG | 8 | (AVERAGE) 0.3 mA |
| | FOOT | 9 | |
| | TRUNK | 0 | |
| | EYEBALLS | A | |
| | PUPILS | B | |
| | NO RESPONSE | X | |
| | TREMOR INCREASED | C | |
| | TREMOR DECREASED | D | |

| | | | | |
|---|---|---|---|---|
| SENSATION | (TINGLING) | TONGUE | E | RELIABILITY |
| | | FACE | F | |
| | | HAND | G | 3 GOOD 0.5 VOLTS OR LESS |
| | | LEG | H | 2 FAIR 0.6 – 1.0 VOLTS |
| | | HALF OF BODY & LIMBS | I | 1 POOR OVER 1.0 VOLTS |
| | | DIZZY | J | |
| | | NAUSEA | K | NOTE: ALL "X" RESPONSES |
| | | NOISE | L | HAVE RELIABILITY OF I |
| | | VISUAL | M | EACH VOLT (AVERAGE) 0.3 mA |
| | (PAIN) | FACE | N | |
| | | ARM | O | |
| | | LEG | P | |
| | (HOT OR COLD) | FACE | Q | |
| | | ARM | R | |
| | | LEG | S | |
| | | NO RESPONSE | X | |

SENSATION TO MECHANICAL STIMULUS . . . . . . . . . . . . . . Y
OPPOSITE CAPSULAR OR SENSORY BORDER . . . . . . . . . . . . . Z

FIG-19

COMPUTER CODING OF RECORDING RESPONSES

ATTENTION UNITS . . . . . . . . . . . . . . . . . . . . . . . . . . . . . . . . . . . . . . . A

NON-EVOKED (RHYTHMIC
AND NON-RYTHMIC) UNITS . . . . . . . . . . . . . . . . . . . . . . . . . . . . . . . . . 1

EVOKED RESPONSES

EVOKED RHYTHMIC
(TREMOR SYNCHRONOUS)

| | | | |
|---|---|---|---|
| DEEP, UNSPECIFIED UNITS . . . . . . . | FACE . . . . . . . . . . . | B . . . . . | 2 |
| (INCLUDING PRESSURE) | HAND . . . . . . . . . . | C . . . . . | 3 |
| | SHOULDER-ARM . . . . . | D . . . . . | 4 |
| | LEG . . . . . . . . . . . | E . . . . . | 5 |
| JOINT UNITS . . . . . . . . . . | WRIST . . . . . . . . . . | F . . . . . | 6 |
| | ELBOW . . . . . . . . . . | G . . . . . | 7 |
| | KNEE . . . . . . . . . . . | H . . . . . | } 8 |
| | ANKLE . . . . . . . . . . | I . . . . . | |
| MUSCLE (OR MOVEMENT) UNITS . . . . | TONGUE . . . . . . . . . | J . . . . . | } 9 |
| | FACE . . . . . . . . . . . | K . . . . . | |
| | HAND . . . . . . . . . . | L . . . . . | } 0 |
| | ARM . . . . . . . . . . . | M . . . . . | |
| | LEG . . . . . . . . . . . | N . . . . . | ⟩ |

CELLS

| | | |
|---|---|---|
| TOUCH UNITS . . . . . . . . . . . | TONGUE . . . . . . . . . | O |
| | FACE . . . . . . . . . . . | P |
| | THUMB . . . . . . . . . | Q |
| | INDEX . . . . . . . . . . | R |
| | OTHER FINGERS . . . . . | S |
| | HAND . . . . . . . . . . | T |
| | ARM . . . . . . . . . . . | U |
| | LEG . . . . . . . . . . . | V |
| | FOOT . . . . . . . . . . | W |
| | TRUNK . . . . . . . . . | X |

BILATERAL (VOLUNTARY) MOVEMENT UNITS . . . . . . . . . . . . . . . . . Z
NOVELTY UNITS . . . . . . . . . . . . . . . . . . . . . . . . . . . . . . . . . . . . . . . Y

DEGREE OF CERTAINTY
3 CERTAIN
2 REASONABLY CERTAIN
1 UNCERTAIN

FIG-20

METHOD AND APPARATUS FOR ARCHIVING AND DISPLAYING ANATOMICO-PHYSIOLOGICAL DATA IN A NORMALIZED WHOLE BRAIN MAPPING AND IMAGING SYSTEM

CROSS-REFERENCE TO RELATED APPLICATIONS

This application is a continuation Ser. No. 08/207,234 filed on Mar. 4, 1994 now abandoned.

This application is a continuation-in-part application of U.S. patent application Ser. No. 07/500,788, entitled *Three-Dimensional Graphics Simulation and Actual Imaging Data Composite Display*, to Hardy, filed on Mar. 28, 1990, now abandoned, which is a continuation-in-part of U.S. patent application Ser. No. 07/290,316, entitled *Method and Apparatus for Video Presentation from a Variety of Scanner Imaging Sources*, to Hardy, filed Dec. 23, 1988, now U.S. Pat. No. 5,099,846, the teachings of both of which are incorporated herein by reference.

This application is also related to U.S. patent application Ser. No. 07/428,242, entitled *Three-Dimensional Laser Localization Apparatus and Method for Stereotactic Diagnoses or Surgery*, to Hardy, et al., filed Oct. 27, 1989, and to U.S. patent application Ser. No. 07/534,975, entitled *Three-Dimensional Computer Graphics Simulation and Computerized Numerical Optimization for Dose Delivery and Treatment Planning*, to Hardy, et al., filed Jun. 8, 1990, the teachings of both of which are incorporated herein by reference.

This is a continuation Ser. No. 07/712,252 filed on Jun. 6, 1991, now abandoned.

BACKGROUND OF THE INVENTION

1. Field of the Invention (Technical Field)

The present invention relates to a method and apparatus for displaying maps of anatomical brain structures, physiological and chemical topography, and other such data in combination with scanned images of individual human brains. The invention produces two-dimensional and three-dimensional displays, with maps proportioned properly according to landmarks in and around the scanned brain. The invention also permits display of a combination of two or more types of brain maps simultaneously and the archiving and cross- referencing of anatomico-physiological data in a normalized whole-brain mapping and imaging environment. This normalized mapping technique further permits the plotting, transposing and interrogation of data from various mapping sources or treatment modalities in the same imaging environment. Such examples also include but are not limited to:

1) Plotting known or scan determined metabolic and/or chemically specific regions or structures of the brain.
2) Plotting known or scan determined psycho-physical regions of the brain and other such data.
3) Plotting and determining the radiation dose to each area or structure of the brain during radiation treatment.
4) Plotting known or scan determined electromagnetic somatotopography of the brain.

2. Background Art

The prior art discloses three primary systems for mapping the human brain, all involving reference to books and charts in order to pinpoint anatomical structures and functions or responses within individual brain scan or other images, such as, but not limited to, computerized axial tomography (CT), magnetic resonance imaging (MRI), radioisotope imaging, and other similar digital imaging systems.

The first primary brain mapping system of the prior art is disclosed by J. Talairach & P. Tournoux, "Co-Planar Stereotaxic Atlas of the Human Brain," (New York; Theieme Medical Publishers; 1988). That book places 133 anatomical structures within a three-dimensional proportional grid subdividing the human brain.

The second system of the prior art is disclosed by G. Schaltenbrand & P. Bailey, *Introduction to Stereotaxis with an Atlas of the Human Brain* (New York, Thieme, 1959), J. M. Van Buren & R. C. Borke, *Variations and Connections of the Human Thalamus* (vols. 1 & 2, New York, Springer, 1972), and G. Schaltenbrand & W. Wahren, *Atlas for Stereotaxy of the Human Brain* (2d ed., Stuttgart, Thieme, 1977). These references consist of magnified photographs of human brainstem slices (including thalamus and lower brainstem regions) wherein subregional or subdivisions of larger structures are indicated by line drawings which represent the microscopic boundaries between such subregions or subdivisions. These mapping systems generally have transparent plastic sheet overlays which contain the line drawings and can be superimposed over the photographs so that such subdivisions can be discerned.

The third system of the prior art is disclosed by T. Hardy, "Stereotactic CT Atlases," ch. 34 of L. D. Lunsford, ed., *Modern Stereotactic Surgery* (Boston, Martinus Nijhoff, 1988). This reference reports subdivisions of the brain by physiological responses according to electrical stimulation or recordings in and about the brain.

With the prior art, a brain surgeon would be required, in planning an operation (regardless whether stereotactic or otherwise), to compare scans of the patient's brain with information from the above references, and would be required to construe certain anatomical structures within the scans based upon visual interrogation of the scans and the references. Such practitioners would also be required to infer or surmise the position of various physiological brain regions. For very precise work, this might involve calculations by hand to correlate the reference brain sizes and shapes with the size and shape of the patient's brain.

SUMMARY OF THE INVENTION (DISCLOSURE OF THE INVENTION)

The present invention presents a method and an apparatus for providing brain map data to a user comprising: digitally archiving brain map data; displaying on a display device one or more brain maps; and manipulating the brain maps on the display device.

In the preferred embodiment, manipulating comprises varying the size, shape, and location of the brain maps on the display device. The preferred embodiment additionally comprises displaying images of an individual patient's brain on the display device, wherein the brain maps are combined with the displayed images of the individual patient's brain to create a composite image on the display device including a two-dimensional overlayed composite image, a three-dimensional transparency composite image, and a three-dimensional image comprising three images of the patient's brain, one in the sagittal plane, one in the horizontal plane, and one in the verticofrontal plane. The brain maps are manipulatable to correspond in location, size, and shape to the images of the individual patient's brain on the display device.

The brain map data may comprise at least one member selected from the group consisting of Talairach-Tournoux anatomical data, Schaltenbrand and Bailey anatomical maps, Van Buren and Borke anatomical maps, Schaltenbrand and Wahren anatomical maps, electrophysiological response data, electromagnetic encephalography (EMEG) data, somatosensory evoked potentials data, electroencephalagram (EEG) data, metabolic brain scanning data, and blood vessel territorial supply data. The brain maps are independently manipulatable to correspond in size, shape, and location to one another on the display device and may be combined with one another to create a composite image on the display device (including two-dimensional overlayed composite image and three-dimensional transparency composite image).

Manipulating may comprise manipulating the brain maps with reference to specified landmarks, including anatomical structures and reference points on a stereotactic frame. The anatomical structures tacked may comprise anterior commissure, posterior commissure, highest surface of parietal cortex, most posterior surface of occipital cortex, most anterior surface of frontal cortex, lowest surface of temporal cortex, left-most lateral surface, right-most lateral surface, thalamic height, fourth ventricle caudal floor fourth ventricle rostral floor, anterior pons wall, intercommissural plane, third ventricle width, lateral ventricle margin, thalamic width, lateral thalamic border, anterior brainstem margin, posterior brainstem margin, brainstem width, lateral brainstem margin. Manipulating may comprise tacking anatomical structures on the display device.

The preferred embodiment further comprises displaying and manipulating one or more simulated brain structures on the display device. The simulated brain structures may be combined with the brain maps to create a composite image on the display device, including a two-dimensional overlayed composite image and a three-dimensional transparency composite image. The simulated brain structures are manipulatable to correspond in location, size, and shape to the brain maps on the display device.

Structures within one of the brain maps on the display device may be selected, whereupon textual information concerning the structure is displayed on the display device, for instance nomenclature for the structure, nomenclature for substructures of the structure, nomenclature for structures containing the structure, medical information concerning the structure, and warnings and advice concerning the structure. Brain maps may be manipulated by enlarging the selected structure on the display device, showing greater detail of the selected structure.

A primary object of the present invention is to permit computer-controlled display of brain scans in combination with appropriately proportioned maps of anatomical brain structures, physiological and chemical topography, and other such data in combination with scanned images of individual human brains.

Another object of the present invention is to permit display of three-dimensional simulations of the locations of anatomical structures and functions, or physiological and chemical responses and functions within a patient's brain.

An additional object of the present invention is to permit cross-correlation and simultaneous display of anatomical brain maps from different prior art brain mapping systems.

Yet another object of the present invention is to permit the archiving of anatomico-physiological data in a normalized brain mapping and imaging system.

A primary advantage of the present invention is that a brain surgeon or other health practitioners may locate anatomical structures, and determine their names and brief descriptions, within a brain scan without consulting a textual reference work.

Another advantage of the present invention is that calculations by hand to position instruments, beams, radioactive dosages, and the like, within a patient's brain are obviated.

An additional advantage of the present invention is that additional mapping data from anatomico-physiological interrogation of the brain can be archived in a normalized brain mapping and imaging system for cross-correlation and future reference.

Other objects, advantages, and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention.

FIGS. 6–10 illustrate the preferred tacking process of the invention;

FIG. 18 illustrates division of the two hemispheres of the brain (left and right) into proportional voxols;

FIGS. 19 and 20 are charts of stimulation and recording data from the diencephalon.

DESCRIPTION OF THE PREFERRED EMBODIMENTS (BEST MODES FOR CARRYING OUT THE INVENTION)

The whole brain mapping, archiving and display apparatus and method of the present invention comprise methods, hardware components and associated software, providing to neurosurgeons, radiologists, or other health practitioners the ability to display patients's brain scans simultaneously with maps of anatomical structures and/or brain functions or responses appropriately proportioned to the particular patient's brain scans. The invention is useful for all operations on the brain and interrogations of the brain's structures and functions, whether or not invasive, both in planning and during execution of operations or interrogations.

Throughout the specification and claims, the following terms are defined as follows: "Tacking" is an alignment process which consists of entering into a computer system the spatial position of a point, object, structure or surface. "Voxol" is a divisional unit of three-dimensional space which consists of either a cube or a parallelpiped. "Ventricles" are central cavities of the brain which constitute normal brain structures around which other constant structures are found. "Brainstem" is the central core structure of the brain, including the thalamus and basal ganglia, which is an upward continuation of the spinal cord. "Three primary brain mapping systems" include the Talairach-Tournoux whole brain proportional system, the brainstem anatomical atlas maps of Schaltenbrand and Bailey, Van Buren and Borke, and Schaltenbrand and Wahren, and the electrophysiological topographical maps of Hardy. "Mapping" is the process of identifying or localizing the position of anatomico-physiological data and structures or regions of the brain in a manner which allows such topography to be discerned and reproducible. "Normalizing" is the process of sizing the brain in a standard and reproducable fashion such that cross-referencing and comparisons are possible.

Figure 3:
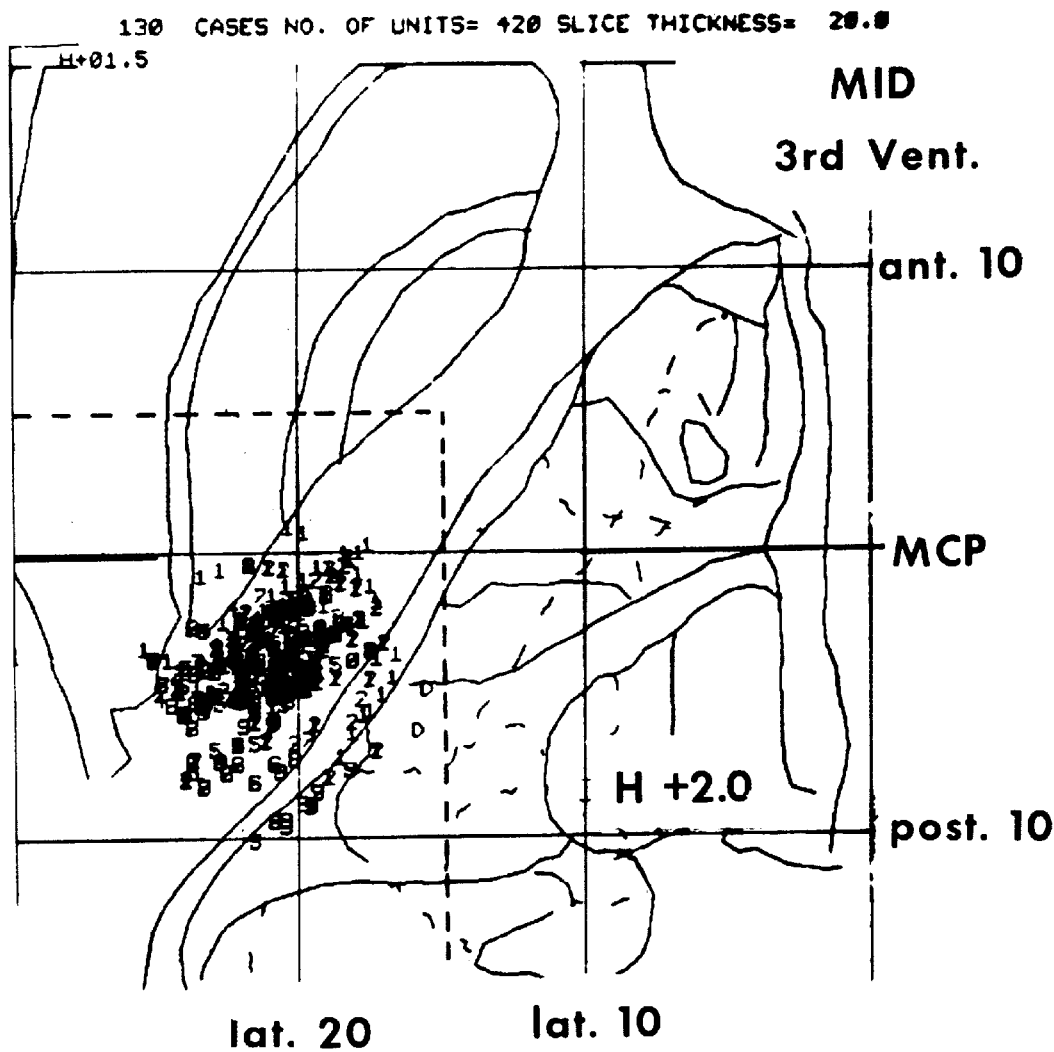
FIG. 3 illustrates a two-dimensional electrophysiological display of the invention.
Figure 4:
FIG. 4 illustrates a two-dimensional cross-correlation display of the invention.
Figure 5:
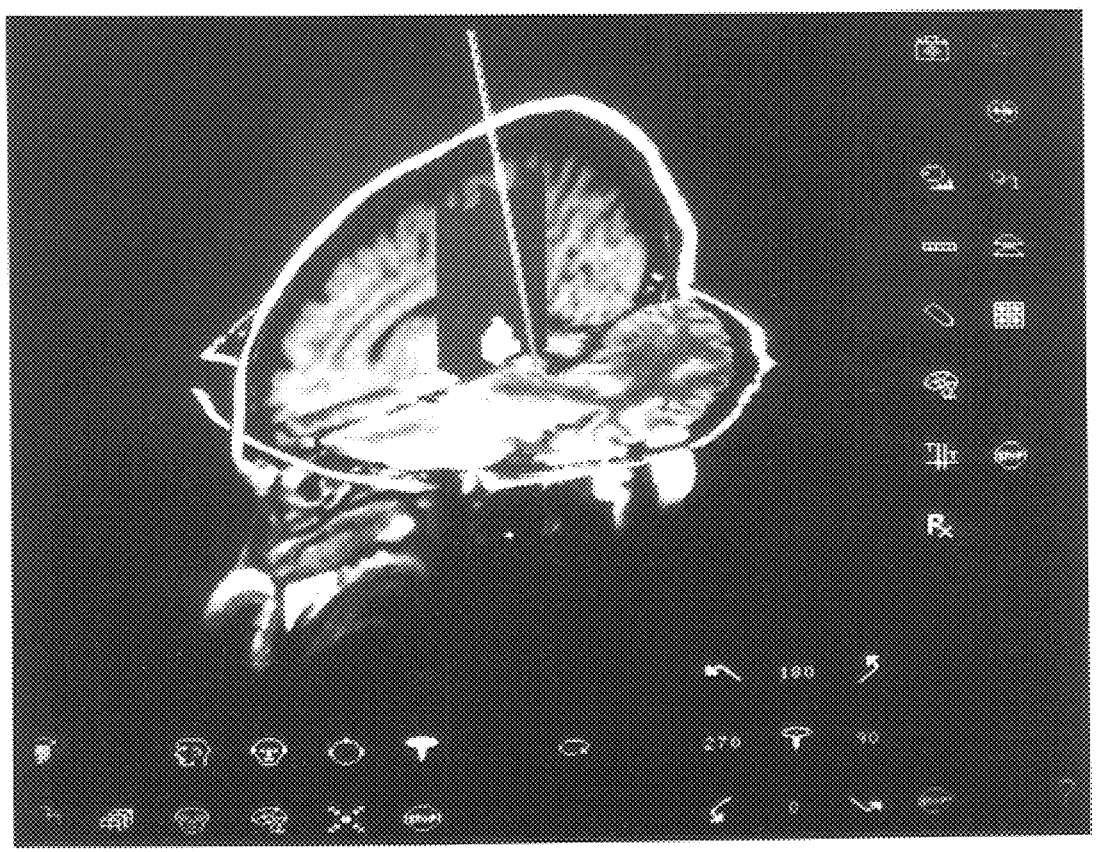
FIG. 5 illustrates a three-dimensional cross-correlation display of the invention.

The preferred embodiment of the present invention permits simultaneous display, manipulation, and/or cross-correlation of brain mapping systems such that data from various mapping techniques can be related to each other in a normalized mapping environment. In each of the mapping systems of the preferred embodiment (the Talairach-Tournoux, brainstem anatomical, and electrophysiological), a common mapping origin of a cartesian coordinate system is constructed about the third ventricle (also the fourth ventricle in the case of the brainstem anatomical and the electrophysiological mapping systems), and the systems are organized in such a manner that they serve as standard referencing systems upon which other anatomico-physiological mapping data can be correlated. As an example, a health practitioner may display a scan image of a particular horizontal slice of a patient's brain. The practitioner may then superimpose an anatomical map showing the positional organization of anatomical structures within the scanned image (FIG. 4). If the anatomical map is not sized properly for the particular patient, the practitioner may execute a resizing procedure to more precisely conform the anatomical map overlays with the particular brain being studied. The practitioner may then display electrophysiological mapping data upon the scan for a particular brain response, for example the location of a stimulus response resulting in contraction of the right thumb (FIG. 3). Both mapping methods (brainstem anatomical and electrophysiological) use the same coordinate reference system and may therefore be combined with each other or with the Talairach-Tournoux method, having the same coordinate reference system, for additional cross correlation and comparison (FIG. 5). In addition, anatomico-physiological data obtained by other authors which use either the same or similar nomenclature and/or similar topography or reference anatomy can be readily cross-correlated and archived in the whole brain mapping, archiving and imaging system.

Figure 21:
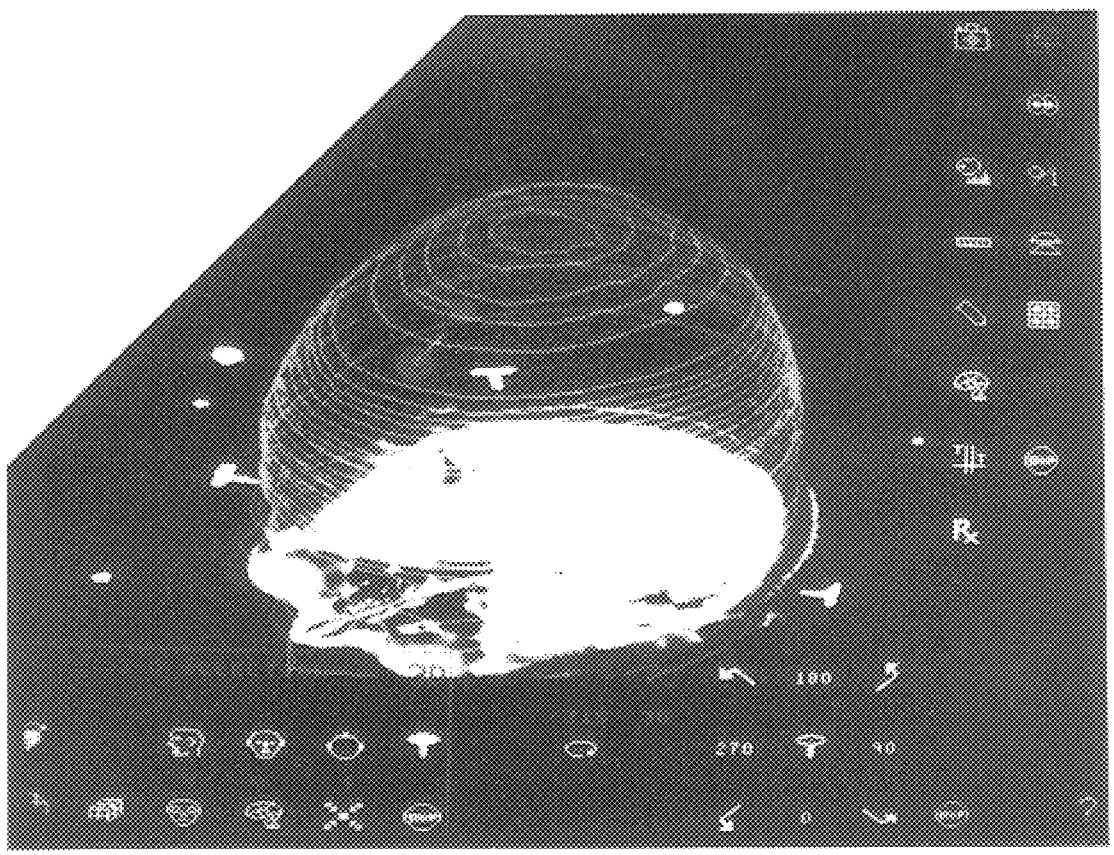
FIG. 21 illustrates a 3-D display of the position of two dipole moments in the brain from EMEG recording.

The invention is readily extendible to additional brain mapping systems developed by the art. For example, electromagnetic encephalography (EMEG) is a new electrophysiological mapping system in which electrical dipole moments can be detected by highly sensitive super-cooled electromagnetic detectors (SQUIDS) (see Sutherling, et al., "The magnetic and electric fields agree with intracranial localizations of somatosensory cortex," 38 Neurology 1705–14 [November 1988]). Such electrical dipole moments can be discerned by these detectors as they are propagated through the brain, such that the electrical moment, for example of a finger movement or other such brain physiological activity, can be discerned against the brain's normal electrical background activity (FIG. 21). The current mapping system is ideal for localizing the anatomical electrophysiological topography of such responses and correlating them with prior knowledge of the brain's anatomico-physiological topography. Similar mapping data from other brain mapping sources, e.g., somatosensory evoked potentials, electroencephalography (EEG), metabolic brain scanning (as in positron emission tomography and SPECT scanning), blood vessel territorial supply (see G. Salamon & Y. P. Huang, *Radiologic Anatomy of the Brain* [New York, Springer-Verlag, 1976]) and other such mapping systems or data may be entered into the preferred embodiment of the present invention. It may then be displayed alone or simultaneously with other maps upon patient brain scans and/or cross-correlated.

Figure 1:
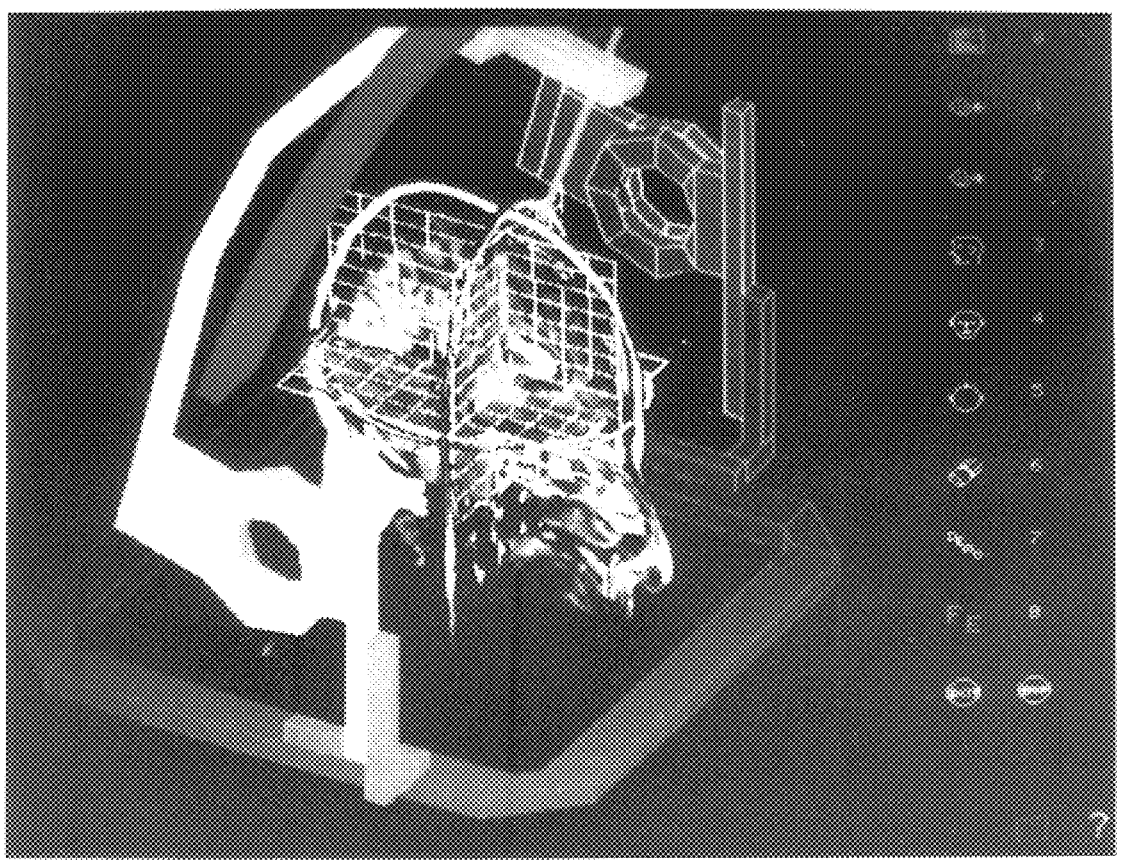
FIG. 1 illustrates a three-dimensional ("3-D") Talairach-Tournoux type display of the invention.
Figure 2A:
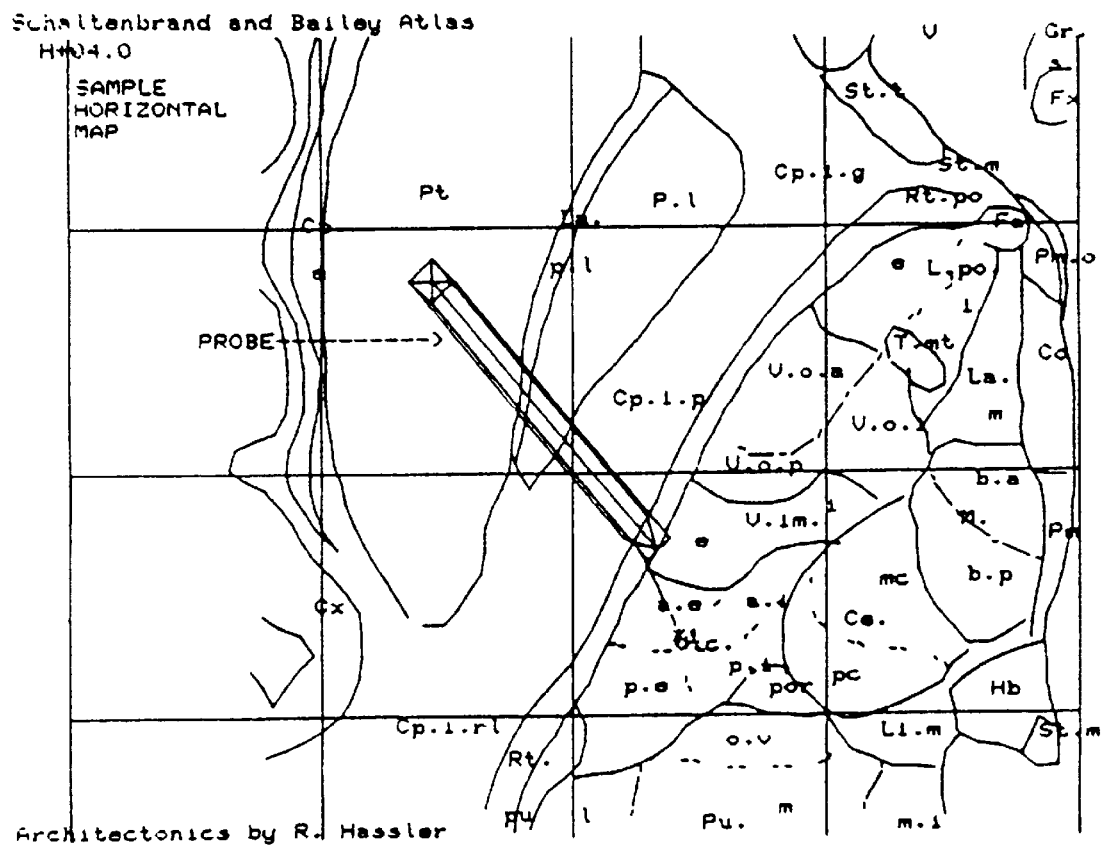
FIG. 2 illustrates a two-dimensional ("2-D") anatomical brain map display of the invention.
Figure 2B:
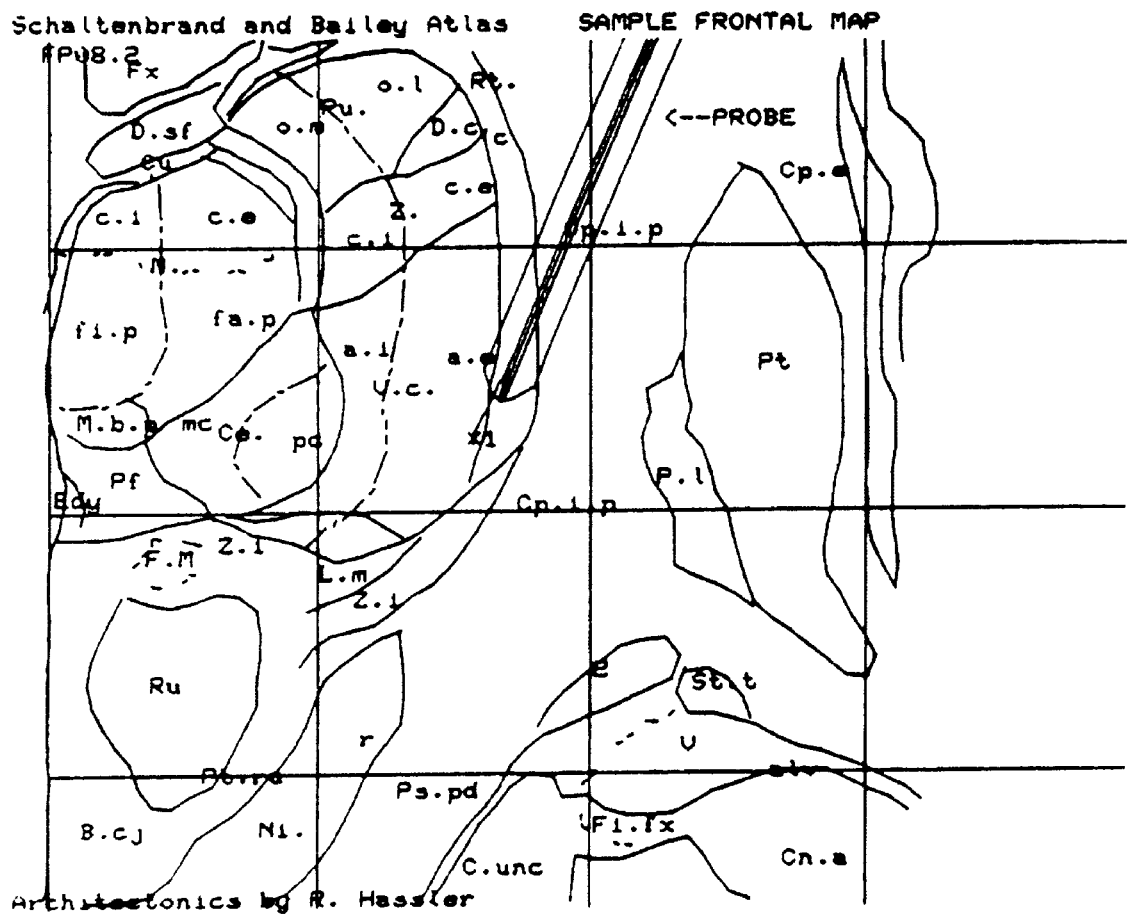
Figure 2C:
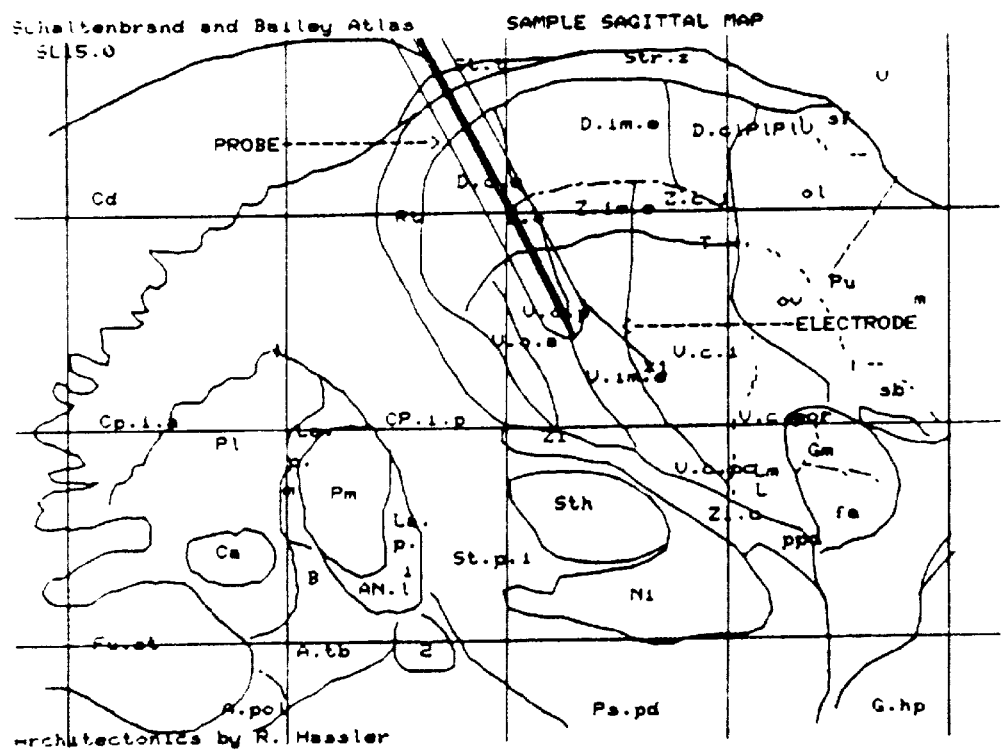
Figure 2D:
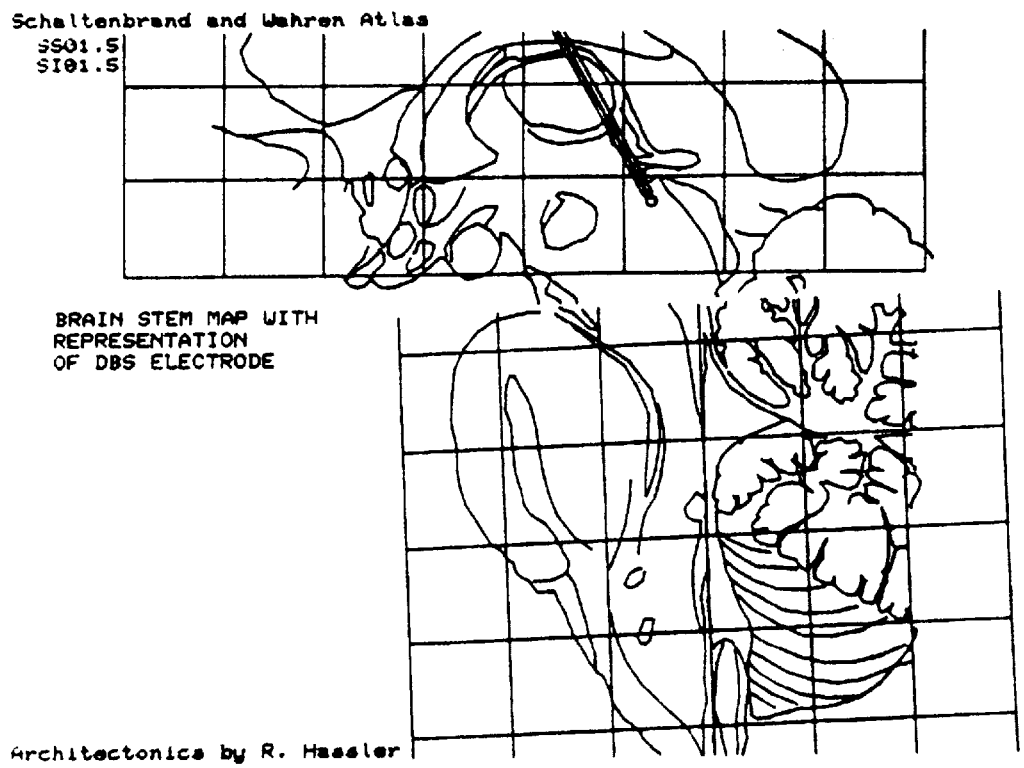

The Talairach-Tournoux system of the prior art divides the brain into a three-dimensional ("3-D") grid system (FIGS. 1 and 18) and is defined according to the maximum dimensions of the brain in the three cartesian planes of space. In two-dimensions, the rectangles of the grid represent the division of the cerebral mass into rectangular parallelepipeds (voxols) in three-dimension. These parallelepipeds in 3-D space are divided as follows:

in the vertical direction, into 12 horizontal sectors, designated 1 through 12, superior to inferior 2.

in the anteroposterior direction, into 9 frontal sectors, designated A to I 4. Additionally, E, which is the area located within the perpendiculars through the anterior commissure ("VAC") and posterior commissure ("VPC"), is divided into 3 sectors 6, allowing a more precise localization of the central gray nuclei.

in the transverse direction, into 4 sagittal sectors, designated a through d in both directions away from the midline 8.

Basing these divisions of the brain on any individual brain proportions, this proportional mapping system creates a normalized general mapping system valid for all brains. Such a system can be adapted to brains of all dimensions.

The prior art discloses an anatomical index identifying many structures (see Talairach & Tournoux at pp. 114–19). For each of the three planes of cartesian coordinate space, the following are indicated in the index:

cortical areas gyri and sulci bundles and ventricles deep gray nuclei, hypothalamic nuclei The index gives the following data:

section: sagittal, frontal, or horizontal small letters (a through d) for sagittal sectors capital letters (A through I) for frontal sectors numbers (1 through 12) for horizontal sectors millimeter distance from the basal line midline for lateral measurement vertical AC line (VAC) for the anteroposterior measurement (+ anterior, − posterior)

basal line AC-PC for the vertical measurement (+ above, − below)

The method and apparatus of the present invention permits computer display of Talairach-Tournoux grid coordinates after brain sizing information has been entered. Once the proportional grid has been defined, any point in the scan can be identified as to the anatomical structures resident in that voxol of brain. This example constitutes a "frameless" coordinate system wherein anatomico-physiological data are localized by identifying the proportional grid voxol (parallelepiped) in which such structures or data are found. If a patient's scanned images are taken with a stereotactic frame or other such reference markers in place, then the coordinate position can also be noted in relationship to the three planes of a cartesian coordinate system or any other coordinate system (for example, polar or cylindrical).

Since anatomical structures are most efficiently named on a computer display using abbreviations, there is also the need for a computer library listing of the international nomenclature. The preferred embodiment of the invention provides such a listing of structures or functions which are noted in the teachings of the primary prior art mapping systems (Talairach-Tournoux, anatomical and electrophysiological).

The method and apparatus of the present invention also permit computer display of anatomical maps corresponding to horizontal, sagittal, and verticofrontal slices of the human brainstem. The line drawings of the prior art displaying brainstem anatomical structures corresponding to various slices of the brain have been digitized (FIG. 2). The digitized maps may be resized to conform to a particular patient's brain by the process of tacking certain anatomical coordinate structures (e.g., anterior commissure, posterior commissure, and other such anatomical landmarks) about the third ventricle and, in the case of lower brainstem maps, coordinate structures (e.g., floor of fourth ventricle, ventricular apex and anterior pontine border) about the fourth ventricle within certain scans taken of the patient's brain. After tacking, the digitized maps are resized before being placed as an overlay display superimposed upon a scan of a brain slice of the patient. This method of mapping creates a normalized anatomical brainstem mapping coordinate system of anatomical overlays valid for all brains.

Additionally, the method and apparatus of the present invention permit computer display of electrophysiological mapping data (FIG. 3). This mapping data consists of a set of known physiological responses to electrical stimulation and recording of the brain (FIGS. 19 and 20). For each physiological response (for example, the topographical position of stimulus or recorded responses representing sensation or movement of a limb or contraction of a muscle [FIG. 3]) data specifying the actual location within a brain where such responses occur upon electrical stimulation and/or recordings thereof is archived. A particular patient's brain may be sized, as with anatomical mapping, and such electrophysiological response data can be displayed upon slices of the patient's brain (FIG. 3) or within voxols of a three-dimensional display (FIG. 5). Such data is plotted and stored as to a normalized coordinate system (previously described above for the associated brainstem anatomical maps and the Talairach-Tournoux method of whole brain proportioning) about the third ventricle. Display of electrophysiological data is important for localizing the anatomical structures associated with certain physiological functions. Furthermore, the display of electrophysiological data is of aid in planning operative procedures in, and physiological and chemical interrogations of, the brain.

Because these prior art mapping systems are based on the same anatomical landmarks (e.g., coordinate structures about the third ventricle which include the anterior commissure and the posterior commissure), it is possible to cross-correlate any one of these mapping systems with one another as well as other mapping systems. It is also possible to transform any such mapping data to other coordinate environments such as stereotactic frame or radiographically calibrated coordinate space, and therefore also display or cross-correlate such mapping data in either a two-dimensional or three-dimensional fashion. Likewise, since most other mapping systems utilize internationally recognized nomenclature for the identification of anatomico-physiological structures and the positional location of such structures are normalized into the whole brain mapping, archiving and imaging environment of the present invention, then it is possible to cross-correlate data from other mapping systems into the imaging environment of the present invention.

The method and apparatus of the present invention store primary indices of anatomical structures and functions, each according to the primary mapping systems, within computer files in the following fashion:

A. Talairach-Tournoux Type System

Each location in the file contains a flag indicating whether the correspondingly numbered structure is found (1) or is not found (0) at that location, as exemplified below:

| location in file | grid location | structure # |
|---|---|---|
| 1 | a | 1 |
| 2 | a | 2 |
| 3 | a | 3 |
| ... | ... | ... |
| 112 | ab | 1 |
| ... | ... | ... |
| 223 | b | 1 |
| ... | ... | ... |

The structure number corresponds to an index into an array of strings (the abbreviations for the name given by the international nomenclature of each structure).

Figure 13:
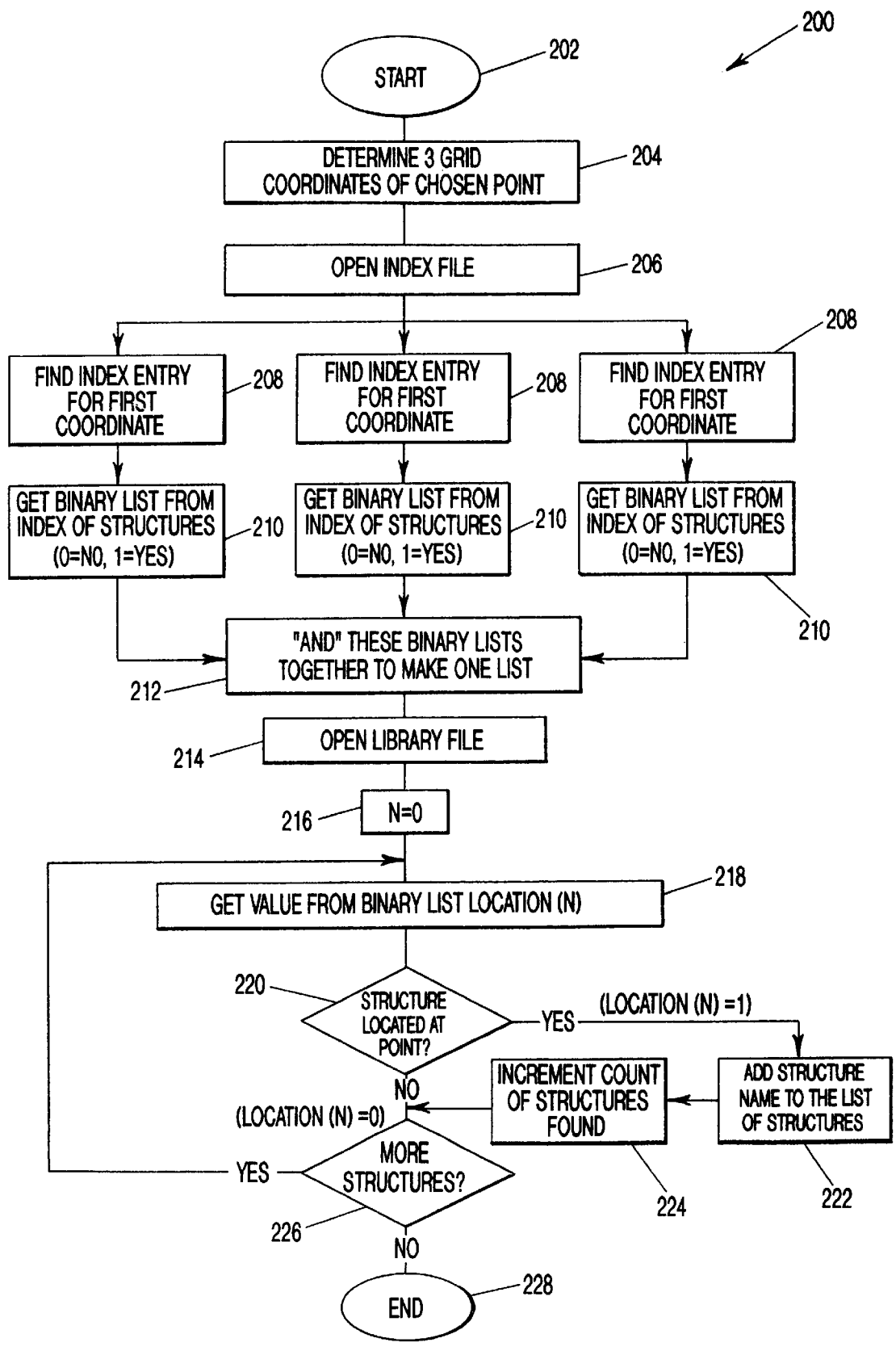

As shown in FIG. 13, searching of the index for anatomical structures in a given grid location 200 (cortical or subcortical area) is accomplished on initiation 202 by directly locating the correct grid locations 204 in the index file 206 and determining which structures are found in each of the three grid coordinates. Once the three grid coordinates (voxol) of a selected point are determined, the structures are determined as follows. The index file is opened 206 and each of the three grid coordinate entries are located and the structure list extracted 208. The list of structures located at each of the three grid coordinates 210 is then compared (by "AND" ing the three lists) and the structures located at the given voxol (located within all three coordinates) are thus determined 212.

Once the binary list of structures at a given point has been determined 214, the structure library file is opened 214. Beginning with the first location in the binary list 216, and for each location 226, a loop is performed, after which the procedure is exited 228. In the loop, the value at location n of the binary list is extracted 218, its binary value determined 220, and if it is 1 then the structure name corresponding to the current location in the binary list is added to a list of structures at the point of interest 222 and the number of structures found is incremented 224.

Figure 14:
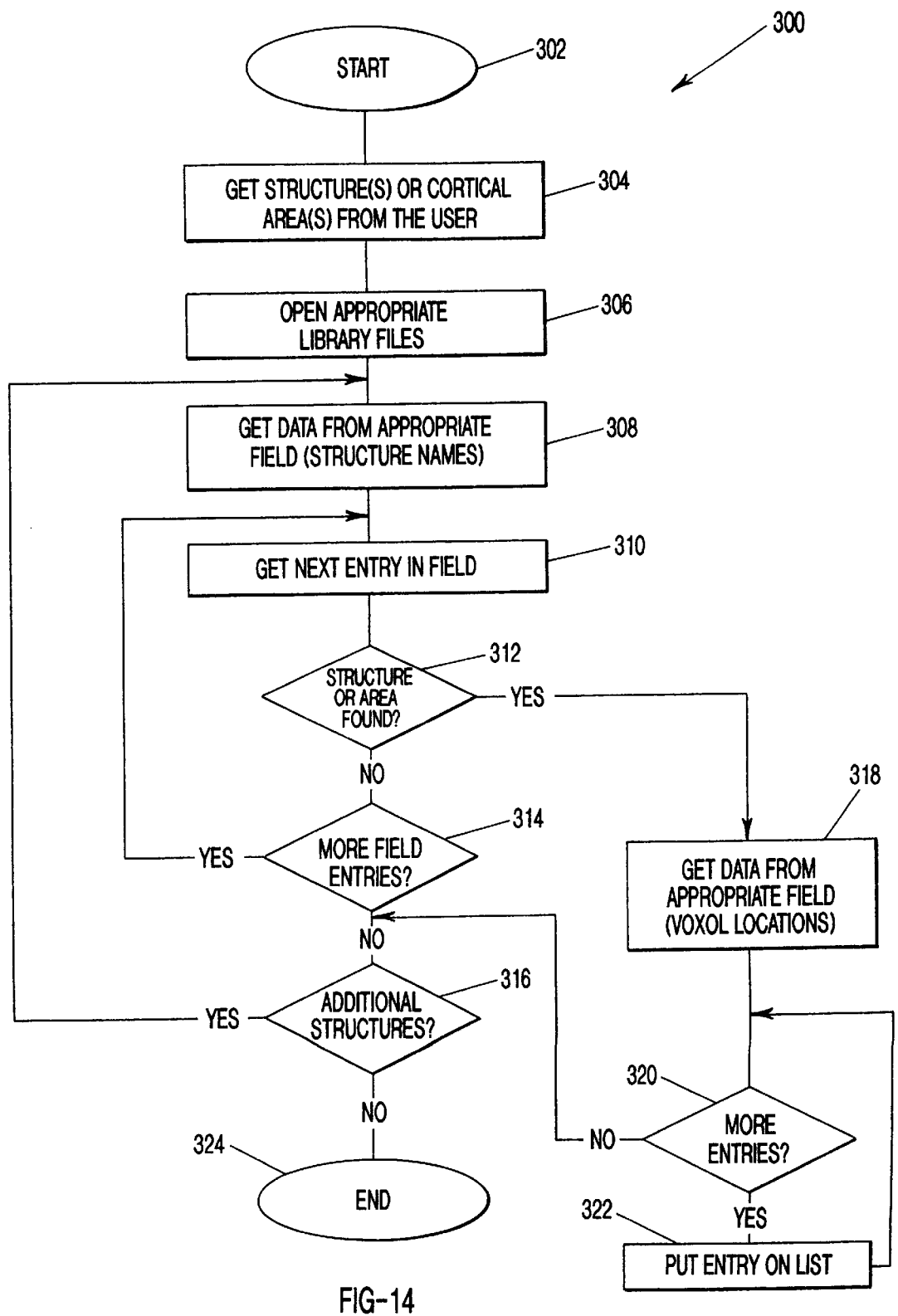

As shown in FIG. 14, searching of the library 300 for the grid coordinates for specified anatomical structures 304 is accomplished 302 by opening the structure library file 306, and looping through the structure library until the file is exhausted 314 or the requested structures are found 316, at which point the procedure is exited 324. Each name field 308 entry 310 is searched for a match with the specified structure name, until the field entries (all given structure names) are exhausted 314. When a structure is found in the library file 312, the voxol locations are extracted from the entry's location field 318 and are placed on a list 322 until exhausted 320.

Figure 15:
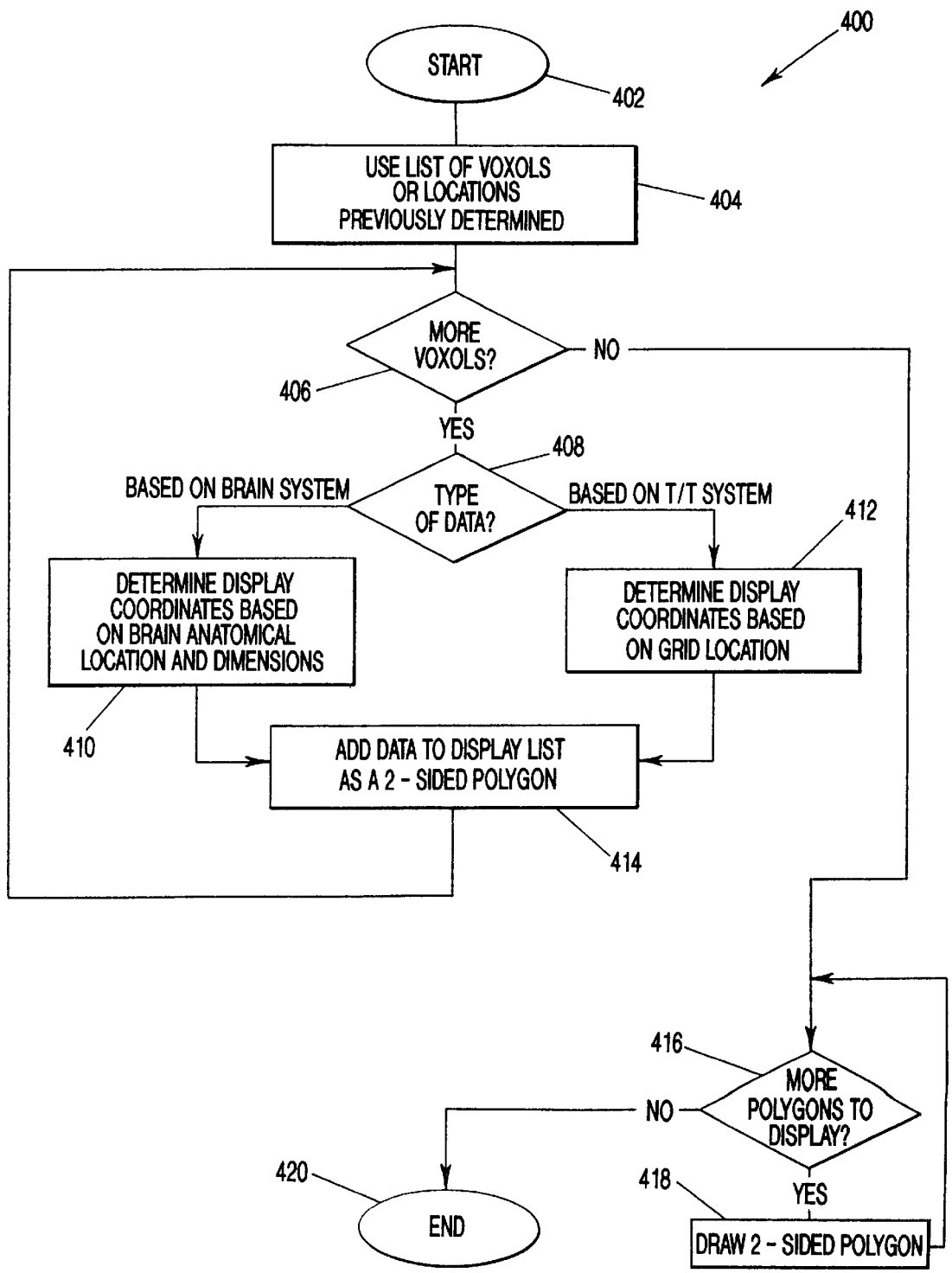

As shown in FIG. 15, structures are displayed 400 once voxol locations have been determined 402 based upon the list of locations compiled 404. For each voxol 406, data is added to a display list of two-sided polygons 414. If the data 408 is based on the Talairach-Tournoux system, display coordinates are determined based on grid location (see FIG. 17). If the data 408 is based on brain anatomical location and dimensions, display coordinates are determined with reference to tacked points 410. The polygons are then displayed 418 until all have been displayed 416, whereupon the display process is complete 420.

Figure 17:
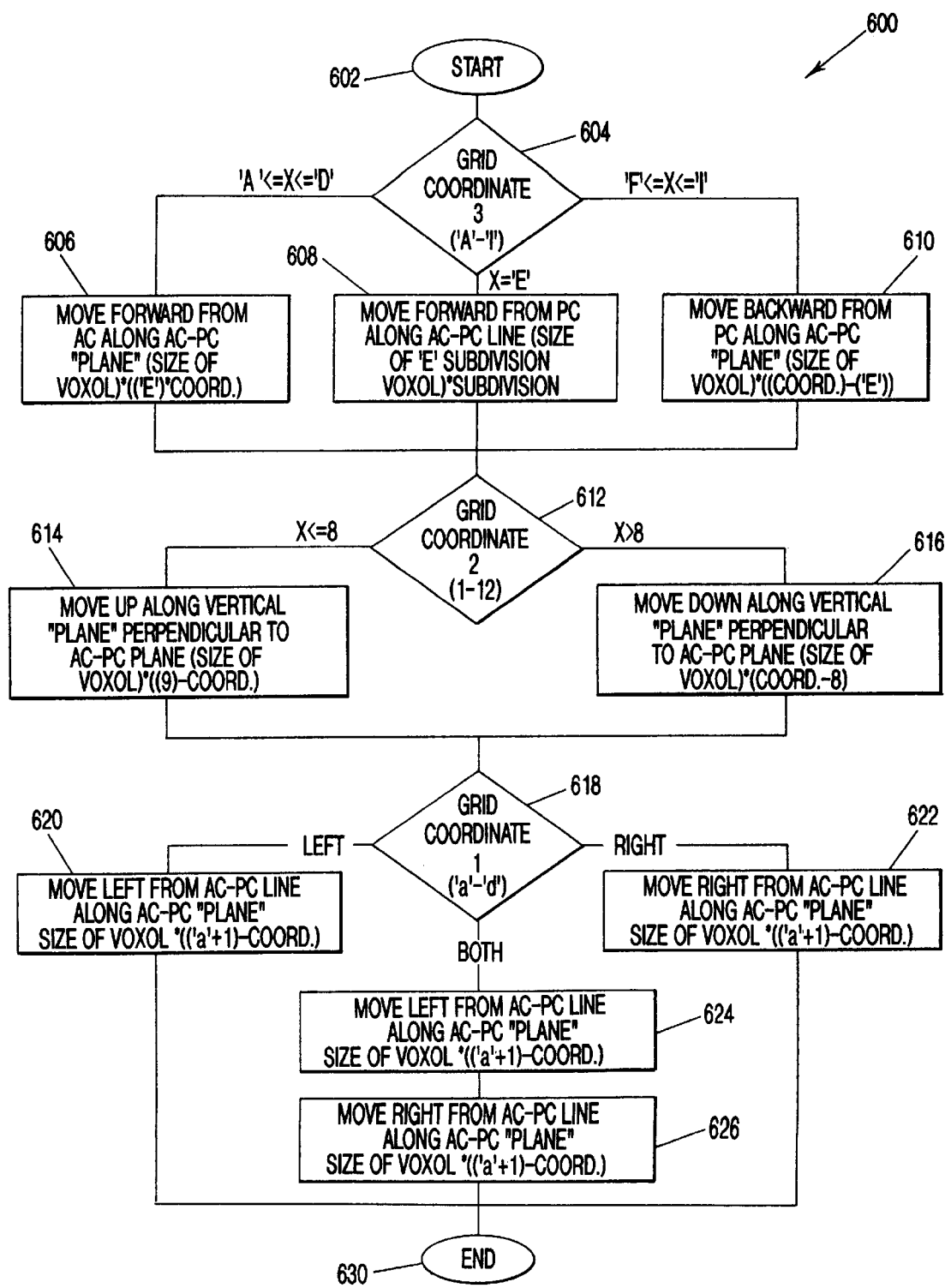

As shown in FIG. 17, to determine the cartesian coordinates of any given Talairach-Tournoux voxol (identified by three Talairach-Tournoux) grid coordinates, i.e., "a-6-D") for display or cross correlation, it is necessary to convert each coordinate into its representative location 600. starting 602 with coordinate 3 604 ('A' through 'I' which divides the brain from anterior to posterior) the anterior-most coordinate of the voxol is determined by moving forward or backward along the AC-PC "plane" (from either the AC or the PC) the appropriate distance. The appropriate distance is based on the grid coordinate which determines the starting point and direction as follows:

'A' through 'D': start at AC and move forward (anterior) 606;

'E': start at PC and move forward (anterior) 608; and

'F' through 'I': start at PC and move backward (posterior) 610.

Once the anterior-posterior location of a voxol region is determined, the vertical (S-I) 612 and horizontal (R-L) 618 locations of the voxol are found in the same manner (614 or 616, and 620 or 622, or 624 and 626) for final localization of the spatial position of the voxol, whereupon the procedure is complete 630.

The anatomical structures selected (as well as the corresponding voxols) and any Talairach-Tournoux defined electrophysiological data selected are stored for access by the invention. Since it is not known ahead of time how many voxols or electrophysiological units need to be displayed, the best data structure for this information is a linked list. This dynamic structure is flexible enough to allow access and display of a large amount of data and to allow for future addition of additional mapping capabilities.

The selection of structures of interest to the brain surgeon is performed much the same way menu questions are selected within the menus disclosed by U.S. patent application Ser. No. 07/500,788. The user simply touches the screen at the structure listing. Each mapping system has a library listing of structures from which these selections can be made. Because of some differences in nomenclature between the prior art atlases, the search performed for any particular structure will be according to a complete listing of all possible spellings or names of a given structure (taken directly from all of the libraries used). Whenever a new mapping system and corresponding library is added, the same structure is used such that the new nomenclature can be immediately accessed and cross-correlated with other atlases or mapping data.

In the preferred embodiment, the method of the present invention requires definition of a coordinate reference system in three-dimensional space, based upon actual brain images acquired in all three views as follows:

sagittal midline image, perpendicular to frontal and horizontal views frontal image passing through the anterior commissure, perpendicular to sagittal and horizontal views horizontal image along the anterior commisure-posterior commissural line, perpendicular to frontal and sagittal views These images represent planes of a three-dimensional cartesian coordinate reference system arranged about the third ventricular core of the brain such that data from the reference coordinate environment can be readily cross-correlated or transformed to or from other reference environments.

Figure 12:
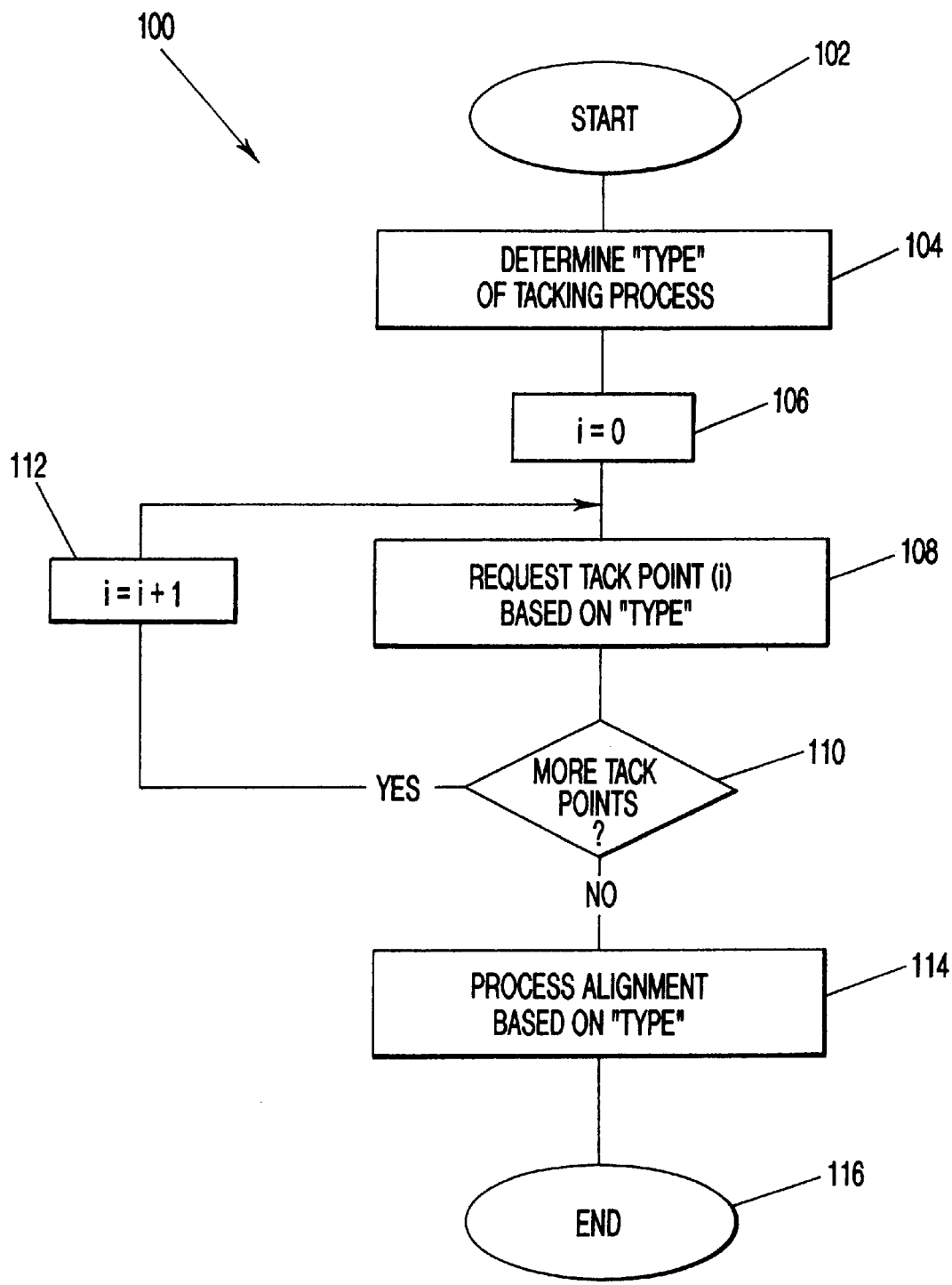
FIGS. 12–17 are flowcharts representing the software embodiment of the invention.

Alignment is achieved by acquiring orthogonal images along the various reference planes of the coordinate system and performing the necessary tacking procedures 100 (FIG. 12). When tacking is initiated 102, the type of tacking needed is determined 104 based upon the mapping system in use. Starting with the first tacking point needed 106, tack points are requested 108 one by one 112 until no more tack points are needed 110. With all points tacked, the appropriate aligament is performed 114 and the procedure terminated 116.

The three-dimensional alignment is as follows for a Talairach-Tournoux alignment:

Sagittal (FIG. 6): On a sagittal midline image the following points must be tacked:

ANTERIOR COMMISSURE 10

POSTERIOR COMMISSURE 12

HIGHEST SURFACE OF PARIETAL CORTEX 14

MOST POSTERIOR SURFACE OF OCCIPITAL CORTEX 16

MOST ANTERIOR SURFACE OF FRONTAL CORTEX 18

LOWEST SURFACE OF TEMPORAL CORTEX 20

Frontal (FIG. 6): On a frontal image which passes through the anterior commissure the following points must be tacked:

ANTERIOR COMMISSURE 22

HIGHEST SURFACE OF PARIETAL CORTEX 24

LOWEST SURFACE OF TEMPORAL CORTEX 26

MOST LATERAL SURFACE (LEFT) 28

MOST LATERAL SURFACE (RIGHT) 30

Horizontal (FIG. 6): On a horizontal image through the inter-commissural plane the following points must be tacked:

ANTERIOR COMMISSURE 32

POSTERIOR COMMISSURE 34

MOST ANTERIOR SURFACE OF FRONTAL CORTEX 36

MOST POSTERIOR SURFACE OF OCCIPITAL CORTEX 38

MOST LATERAL SURFACE (LEFT) 40

MOST LATERAL SURFACE (RIGHT) 42

Figure 16:
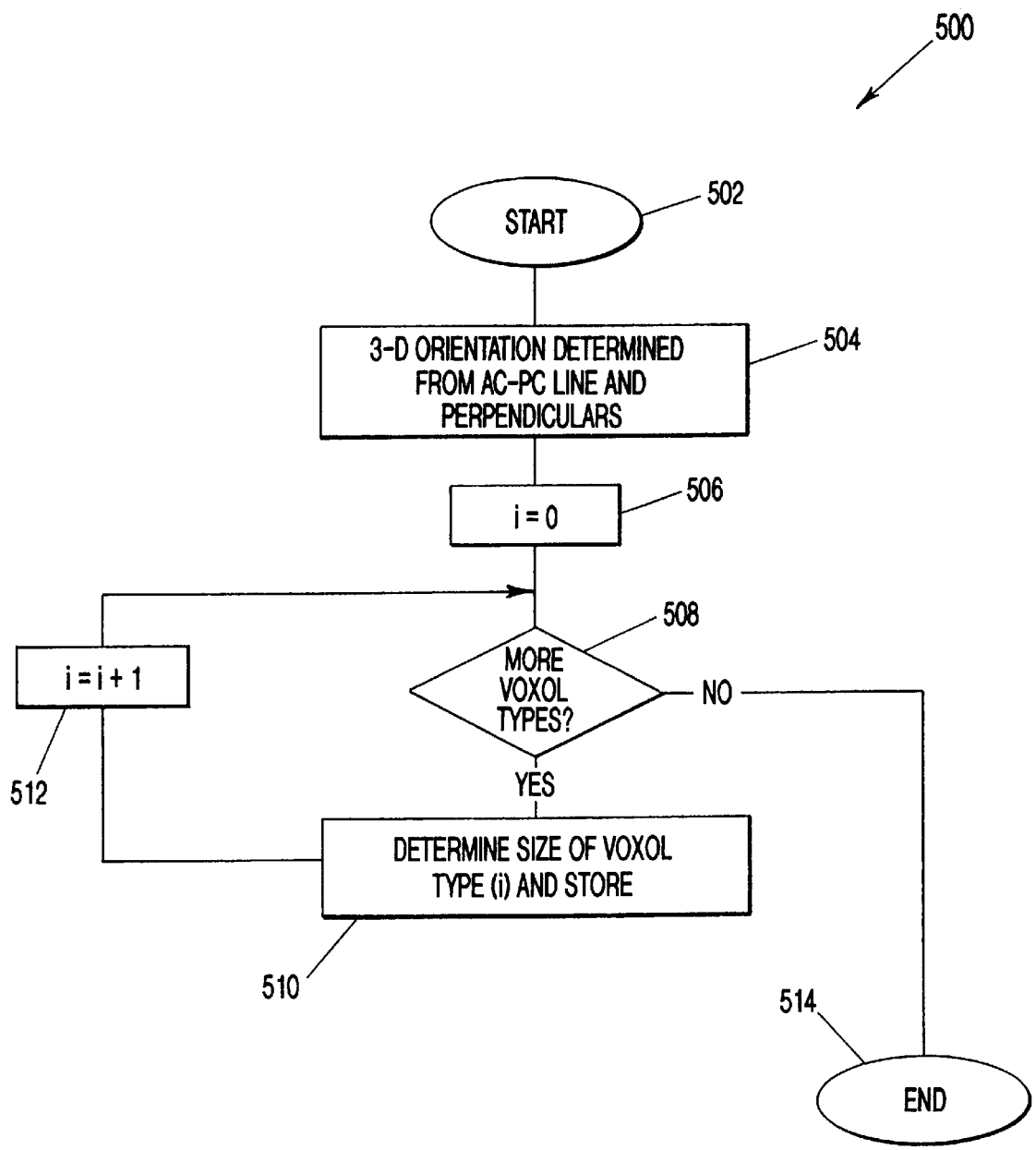

Once tacking is completed, the method of the invention can determine the three-dimensional proportional voxols (and their associated Talairach-Tournoux grid coordinate system as well as the relationship of this coordinate system to any stereotactic frame or radiological reference system which may be in use) (FIG. 16) 500 and the anatomical brain coordinates according to the Talairach-Tournoux method. The normalization process preferably occurs as follows: Once all of the tack points are entered 100 (FIG. 12), a procedure is invoked 502 whereby the three-dimensional orientation of the normalized system is determined from the AC-PC plane (and the perpendiculars of this plane) 504. With this orientation known, the voxol size is determined 510 for each different area of the Talairach-Tournoux system (starting with the first area 506 and iterating 512 until the areas are exhausted 508 and 514) as follows:

'A'–'D': area anterior of the vertical anterior commissure (VAC)

'E$_1$', 'E$_2$', 'E$_3$': area between the vertical anterior commissure (VAC) and the vertical posterior commissure (VPC)

'F'–'I': area posterior of the vertical posterior commissure (VPC)

1–8: area superior to the anterior commissure-posterior commissural plane (AC-PC)

9–12: area inferior to the anterior commissure-posterior commissural plane (AC-PC)

'a'–'d': area to the left and right of the anterior commissure-posterior commissural line (AC-PC)

The voxol size is determined 510 by taking the limits of each area and dividing by the appropriate number of voxols. All such determinations are based on the three-dimensional orientation of the anterior commissure-posterior commissural line and/or plane (AC-PC).

B. Brainstem Anatomical and Electrophysiological Marpina Systems

Figure 7:
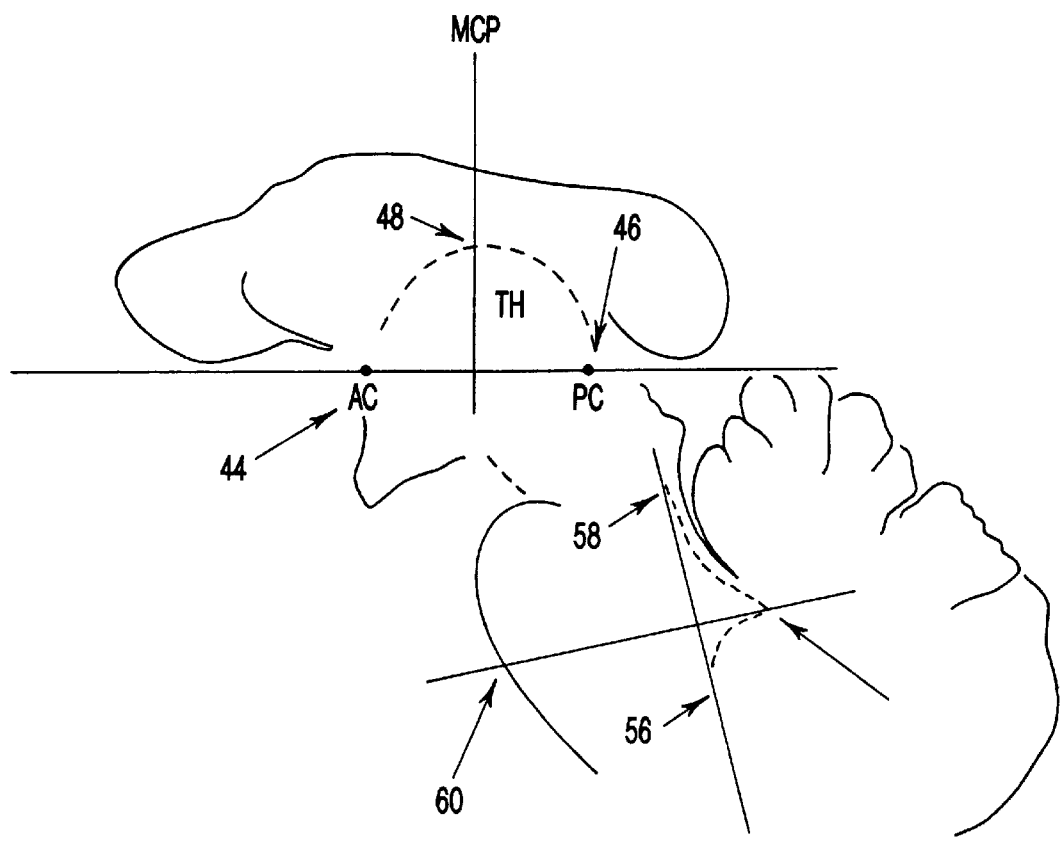
Figure 8:
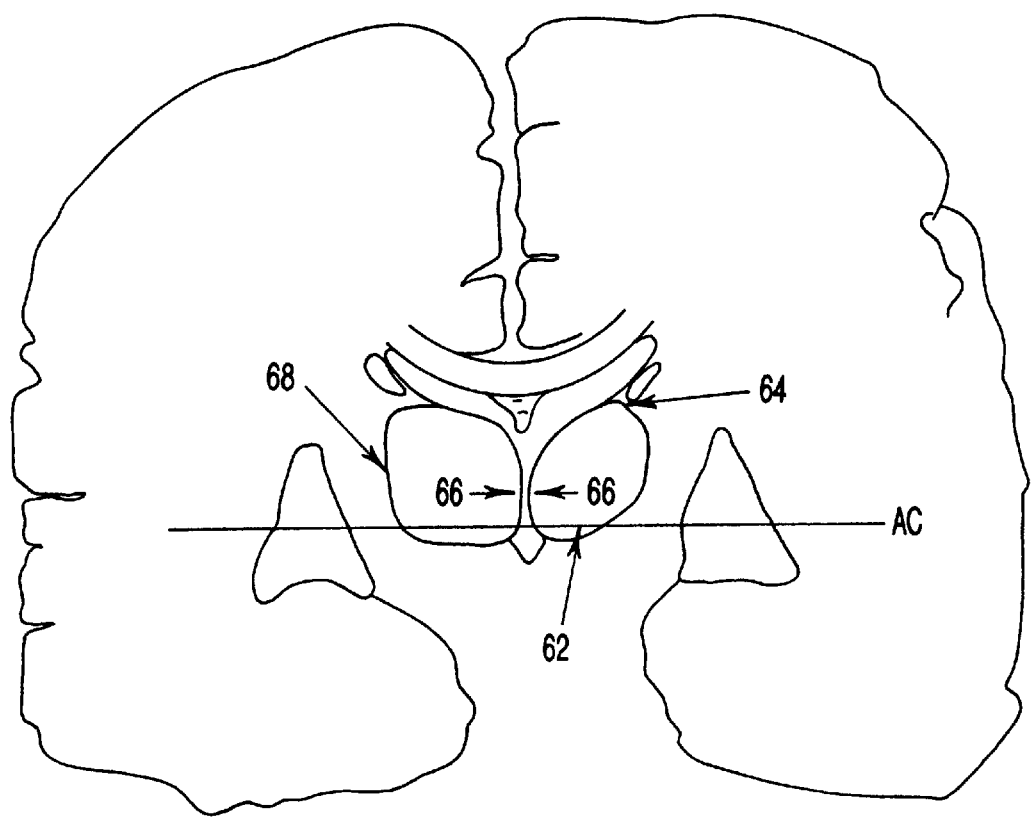
Figure 9:
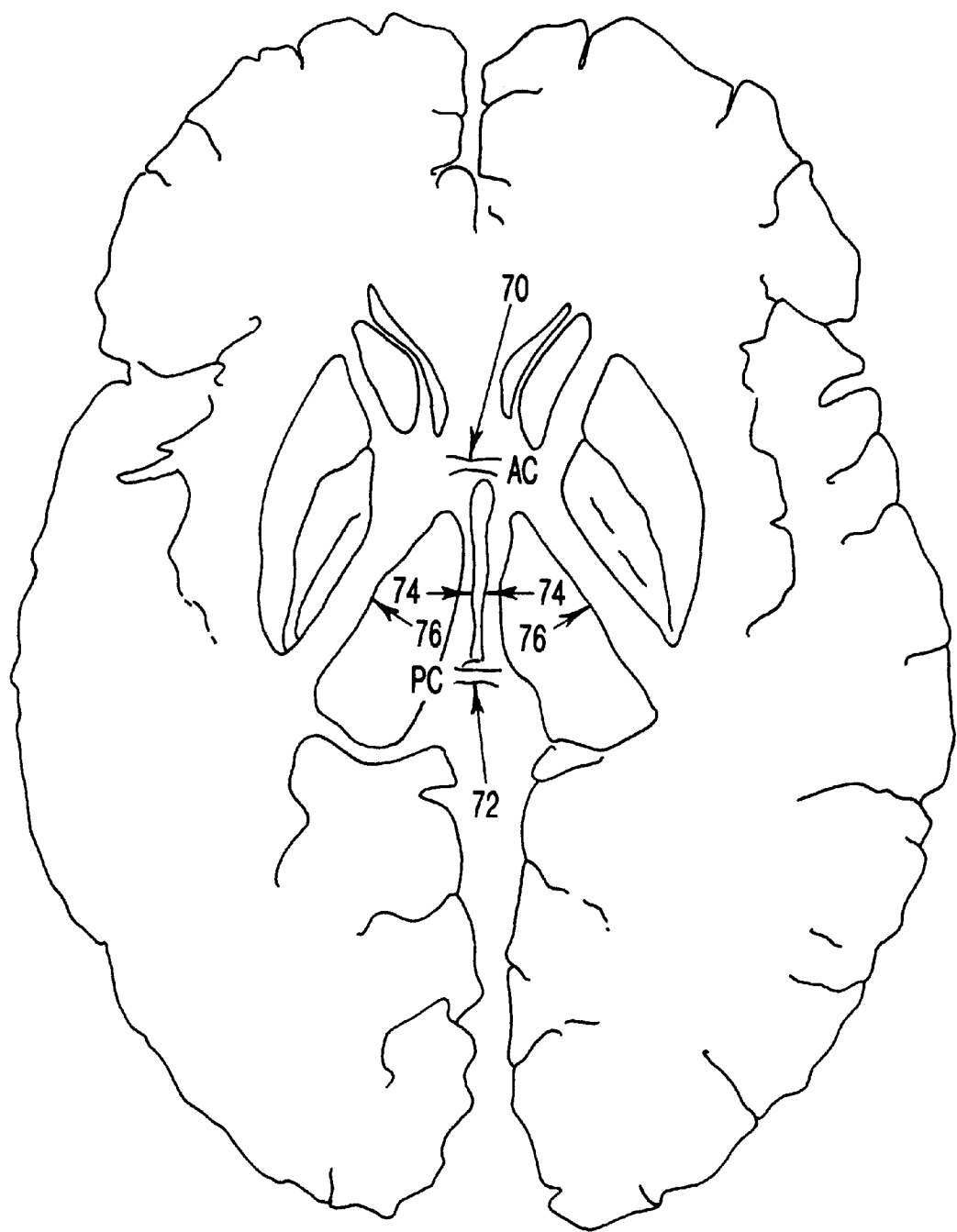
Figure 10:
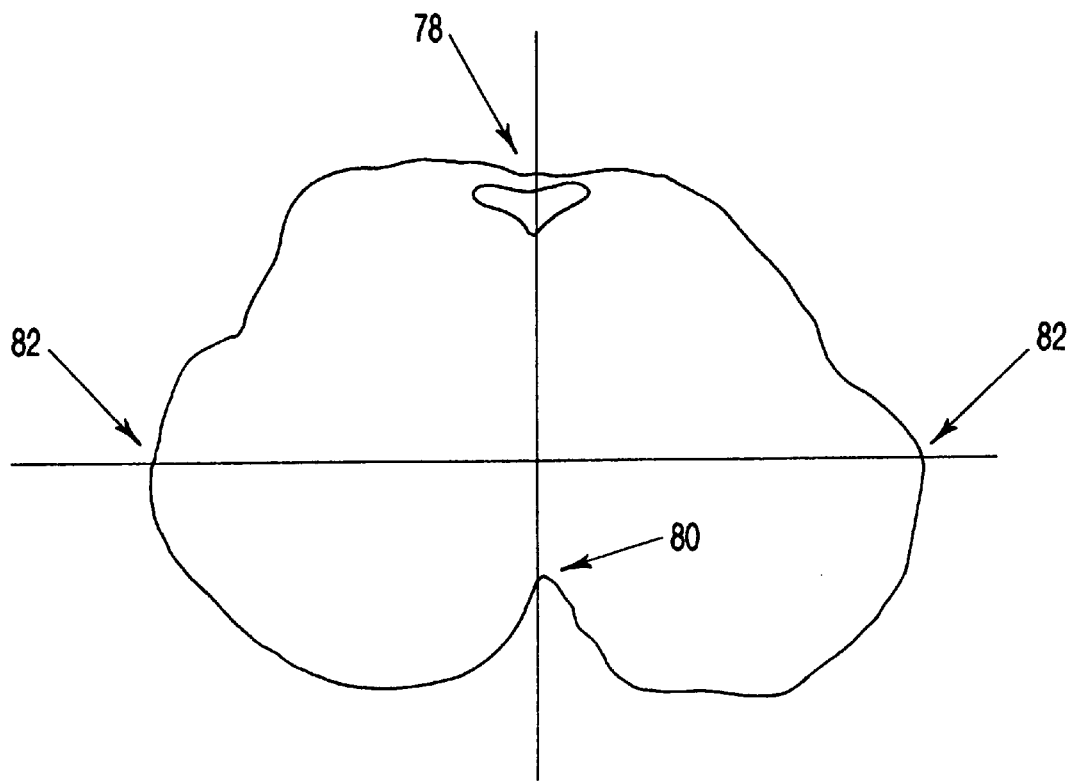

For the use of brainstem anatomical and electrophysiological brain maps, a complete two-dimensional alignment or three-dimensional alignment must also be performed for display. The images should be along the same planes as used for the above noted Talairach-Tournoux alignments. Depending on the digitized maps used (see atlases referenced in parentheses below), the following structures must be tacked in the following planes:

Sagittal (FIG. 7):
Upper brainstem (Schaltenbrand & Bailey and Van Buren & Borke):
ANTERIOR COMMISSURE 44
POSTERIOR COMMISSURE 46
THALAMIC HEIGHT 48
Upper & lower brainstem (Schaltenbrand & Wahren):
ANTERIOR COMMISSURE 44
POSTERIOR COMMISSURE 46
THALAMIC HEIGHT 48
FOURTH VENTRICLE CAUDAL FLOOR 56
FOURTH VENTRICLE ROSTRAL FLOOR 58
ANTERIOR PONS WALL 60
Frontal (FIG. 8):
(Schaltenbrand & Bailey and Van Buren and Borke):
INTERCOMMISSURAL PLANE 62
THALAMIC HEIGHT 64
THIRD VENTRICLE WIDTH/LATERAL VENTRICLE MARGIN 66
THALAMIC WIDTH/LATERAL THALAMIC BORDER 68
Horizontal (FIG. 9):
Upper brainstem (Schaltenbrand & Bailey and Van Buren & Borke):
ANTERIOR COMMISSURE 70
POSTERIOR COMMISSURE 72
THIRD VENTRICLE WIDTH/LATERAL VENTRICLE MARGIN 74
THALAMIC WIDTH/LATERAL THALAMIC BORDER 76
Lower brainstem (FIG. 10) (Schaltenbrand & Wahren):
ANTERIOR BRAINSTEM MARGIN 78
POSTERIOR BRAINSTEM MARGIN 80
BRAINSTEM WIDTH/LATERAL BRAINSTEM MARGINS 82

Once tacking is completed, the method of the invention can scale all structures based on their relationship to the anatomical landmarks which have been tacked on an alignment procedure and other map data from other authors can be proportioned, scaled or referenced in a like manner for cross-correlation.

These map alignments give normalized brain coordinate information necessary for the cross-correlation of different mapping systems. This permits accurate combinations (multiple overlays) of different mapping data superimposed upon actual brain scans. The present invention thus is useful for simultaneously displaying a plurality of different sets of mapping data upon a brain scan image (FIGS. 3 and 4). Other mapping systems can be cross-correlated with maps in the present invention, for example but not limited to:

1. Psycho-physiological anatomical topography (see G. Schaltenbrand & A. E. Walker, eds., *Stereotaxy of the Human Brain: Anatomical, Physiological and Clinical Applications*, p. 572 (2d rev. ed., New York, Thieme, 1982);

2. Thalamocortical projection areas (according to Talairach & Tournoux);

3. Brain vascular territorial distribution (according to Salamon and Huang); and 4. Commonly used stereotactic therapeutic lesion sites (according to Schaltenbrand & Walker at pp. 5–7).

In each case a library is created such that mapping data is localized to specific regions of the brain which are readily identifiable according to Brodmann's numerical topography of the brain (see K. Brodmann, *Vergleichende Lokalisationslehre der Grosshirnrinde* [Barth, Leipzig, 1909]) or recognized named anatomical structures (for example, internationally recognized brain nomenclature of the three prior art mapping systems discussed in depth herein). Such brain topography is also resident in the libraries of the present invention's embodiment and data gathered from anatomico-physiological mapping or interrogation of the brain can be archived and cross-correlated in its normalized brain mapping and imaging environment. For example, data from EMEG, EEG, pre-operative and post-operative localization recordings and many other such similar mapping data can be added to the system for archiving and cross referencing (see FIGS. 3, 4, 5, and 21).

Figure 11:
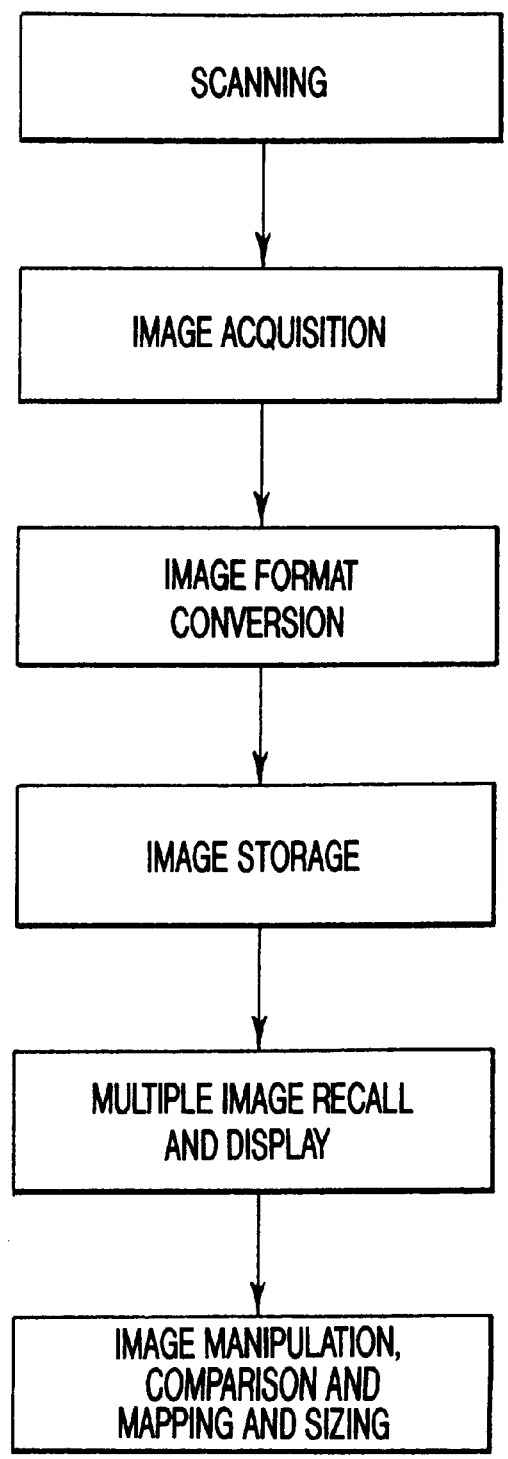
FIG. 11 is a block diagram of the preferred embodiment of the method of the present invention.

FIG. 11 illustrates the preferred method of the invention at the highest level of abstraction. Images are scanned, acquired, converted to an appropriate storage format, stored, retrieved and multiply displayed, compared and manipulated, and sized or proportioned for mapping.

The preferred embodiment of the method and apparatus of the present invention is thus useful to display any combination of normalized brain mapping data together with scans of particular patients' brains. Neurosurgeons or other such health practitioners no longer have to approximate locations of structural and functional areas of the brain, or employ textual reference works, while planning for or executing brain operations. By employing the present invention, such health practitioners may simulate, for example, the insertion of a probe and check which structures and functional areas will be affected by the probe's proposed trajectory. If an unexpected response occurs during an operation, the practitioner has quick access to needed information concerning the response using mapping data superimposed upon scans of the affected areas of the actual patient's brain.

Although the invention has been described with reference to these preferred embodiments, other embodiments can achieve the same results. Variations and modifications of the present invention will be obvious to those skilled in the art and it is intended to cover in the appended claims all such modifications and equivalents.

What is claimed is:

1. A method for providing brain map data to a user comprising the steps of:
   a) scanning at least one brain with at least one of a plurality of scanners and thereby obtaining an image of the at least one brain;
   b) digitally archiving brain map data;
   c) displaying on a display device one or more brain maps;
   d) providing by computer for at least one manipulation selected from the group consisting of movement, resizing, and reshaping of the brain maps on the display device to correspond to a display of the image of the at least one brain on the display device;
   e) organizing the brain maps and brain map data into a three dimensional normalized brain mapping and reference system by tacking in three dimensions anatomical reference points internal to the brain maps and brain map data and determining voxel size, thereby permitting appropriate resizings of the brain maps, brain map data, and the image of the at least one brain once the same anatomical reference points are tacked on the image of the at least one brain;
   f) plotting, transposing, cross-referencing, and interrogating the brain maps and brain map data in the normalized brain mapping and reference system;
   g) combining the brain maps with the displayed image of the at least one brain to create a composite image on the display device;
   h) displaying and manipulating one or more simulated brain structures on the display device; and
   i) combining the simulated brain structures with the brain maps to create a composite image on the display device.

2. The method of claim 1 wherein the step of providing for at least one manipulation comprises the step of varying a size of the brain maps on the display device.

3. The method of claim 1 wherein the step of providing for at least one manipulation comprises the step of varying a shape of the brain maps on the display device.

4. The method of claim 1 wherein combining the brain maps with the displayed images comprises creating a two-dimensional overlayed composite image.

5. The method of claim 1 wherein combining the brain maps with the displayed images comprises creating a three-dimensional transparency composite image.

6. The method of claim 1 wherein combining the brain maps with the displayed images comprises creating a three-dimensional image comprising three images of the at least one brain, one in a sagittal plane, one in a horizontal plane, and one in a verticofrontal plane.

7. The method of claim 1 wherein digitally archiving brain map data comprises digitally archiving at least one member selected from the group consisting of Talairach-Tournoux anatomical data, Schaltenbrand and Bailey anatomical maps, Van Buren and Borke anatomical maps, Schaltenbrand and Wahren anatomical maps, electrophysiological response data, electromagnetic encephalography (EMEG) data, somatosensory evoked potentials data, electroencephalogram (EEG) data, metabolic brain scanning data, and blood vessel territorial supply data.

8. The method of claim 1 wherein combining the simulated brain structures with the brain maps comprises creating a two-dimensional overlayed composite image.

9. The method of claim 1 wherein combining the simulated brain structures with the brain maps comprises creating a three-dimensional transparency composite image.

10. The method of claim 1 wherein displaying and manipulating one or more simulated brain structures comprises manipulating the simulated brain structures to correspond in location, size, and shape to the brain maps on the display device.

11. The method of claim 1 wherein the step of plotting, transposing, cross-referencing and interrogating the brain maps and brain map data in the normalized brain mapping and reference system comprises the step of plotting, transposing, cross-referencing and interrogating mapped data from various mapping sources.

12. The method of claim 1 wherein the step of plotting, transposing, cross-referencing and interrogating the brain maps and brain map data in the normalized brain mapping and reference system comprises the step of plotting, transposing, cross-referencing and interrogating mapped data from various treatment modalities.

13. The method of claim 1 wherein the step of plotting, transposing, cross-referencing and interrogating the brain maps and brain map data in the normalized brain mapping and reference system comprises the step of plotting, transposing, cross-referencing and interrogating mapped data from known metabolic regions of the brain.

14. The method of claim 1 wherein the step of plotting, transposing, cross-referencing and interrogating the brain maps and brain map data in the normalized brain mapping and reference system comprises the step of plotting, transposing, cross-referencing and interrogating mapped data from chemically specific regions of the brain.

15. The method of claim 1 wherein the step of plotting, transposing, cross-referencing and interrogating the brain maps and brain map data in the normalized brain mapping and reference system comprises the step of plotting, transposing, cross-referencing and interrogating mapped data from electromagnetic somatotopography of the brain.

16. The method of claim 1 wherein the step of plotting, transposing, cross-referencing and interrogating the brain maps and brain map data in the normalized brain mapping and reference system comprises the step of plotting, transposing, cross-referencing and interrogating mapped data from predetermined psychophysical regions of the brain.

17. The method of claim 1 wherein the step of plotting, transposing, cross-referencing and interrogating the brain maps and brain map data in the normalized brain mapping and reference system comprises the step of plotting, transposing, cross-referencing and interrogating mapped data from the at least one patient's brain at different times.

18. The method of claim 1 wherein the step of plotting, transposing, cross-referencing and interrogating the brain maps and brain map data in the normalized brain mapping and reference system comprises the step of plotting, transposing, cross-referencing and interrogating mapped data from a plurality of individual patient's brains.

19. The method of claim 1 wherein the step of plotting, transposing, cross-referencing and interrogating the brain maps and brain map data in the normalized brain mapping and reference system comprises the step of plotting, transposing, cross-referencing and interrogating mapped data from a plurality of stereotactic apparatuses.

20. The method of claim 1 wherein the step of displaying on a display device further comprises the step of displaying brain anatomical substructures in two-dimensional format.

21. The method of claim 1 wherein the step of displaying on a display device further comprises the step of displaying brain anatomical substructures in three-dimensional format.

22. The method of claim 1 further comprising the step of generating a video presentation of images of the at least one brain.

23. The method of claim 22 wherein said means for generating a video presentation of the images comprises the steps of:
   a) acquiring image data from at least one imaging source;
   b) deriving a plurality of image data subsets from the image data; and
   c) displaying and manipulating selected image subsets of said plurality of image data subsets independently of other image data subsets of said plurality of image data subsets.

24. The method of claim 1 further comprising displaying images of an individual brain on the display device.

25. The method of claim 24 wherein displaying images of an individual brain on the display device comprises manipulating the brain maps to correspond in location, size, and shape to the images of the individual patient's brain on the display device.

26. The method of claim 1 further comprising selecting a structure within one of the brain maps on the display device.

27. The method of claim 26 further comprising displaying textual information concerning the structure on the display device.

28. The method of claim 27 wherein displaying textual information concerning the structure comprises displaying at least one member selected from the group consisting of nomenclature for the structure, nomenclature for substructures of the structure, nomenclature for structures containing the structure, medical information concerning the structure, and warnings and advice concerning the structure.

29. The method of claim 1 wherein manipulating the brain maps on the display device comprises independently manipulating the brain maps to correspond in size, shape, and location to one another on the display device.

30. The method of claim 29 wherein independently manipulating the brain maps comprises combining the brain maps with one another to create a composite image on the display device.

31. The method of claim 30 wherein combining the brain maps with one another comprises creating a two-dimensional overlayed composite image.

32. The method of claim 30 wherein combining the brain maps with one another comprises creating a three-dimensional transparency composite image.

33. The method of claim 1 wherein manipulating the brain maps on the display device comprises manipulating the brain maps with reference to specified landmarks.

34. The method of claim 33 wherein manipulating the brain maps with reference to specified landmarks comprises manipulating the brain maps with reference to at least one member selected from the group consisting of anterior commissure, posterior commissure, highest surface of parietal cortex, most posterior surface of occipital cortex, most anterior surface of frontal cortex, lowest surface of temporal cortex, left-most lateral surface, right-most lateral surface, thalamic height, fourth ventricle caudal floor, fourth ventricle rostral floor, anterior pons wall, intercommissural plane, third ventricle width, lateral ventricle margin, thalamic width, lateral thalamic border, anterior brainstem margin, posterior brainstem margin, brainstem width, lateral brainstem margin.

35. The method of claim 33 wherein manipulating the brain maps with reference to specified landmarks comprises manipulating the brain maps with reference to anatomical structures and reference points on a stereotactic frame.

36. The method of claim 35 wherein manipulating the brain maps with reference to anatomical structures and reference points on a stereotactic frame comprises tacking the anatomical structures on the display device.

37. A method for providing brain map data to a user comprising the steps of:
   a) scanning at least one individual brain with at least one of a plurality of scanners from the group consisting of computerized axial tomography (CT) scanners, nuclear magnetic resonance (NMR) scanners, positron emission tomography (PET) scanners, isotope scanners, digital subtraction angiography (DSA) scanners, and X-ray scanners;
   b) digitally archiving brain map data;
   c) displaying on a display device one or more brain maps;
   d) providing by computer for at least one manipulation selected from the group consisting of positioning, resizing, and reshaping of the brain maps on the display device to correspond to a display of a brain scan of the brain on the display device;
   e) organizing the brain maps and brain map data into a three-dimensional normalized brain mapping and reference system by tacking in three dimensions anatomical reference points internal to the brain maps and brain map data and determining voxel size, thereby permitting appropriate resizings of the brain maps, brain map data, and the image of the at least one brain once the same anatomical reference points are tacked on the image of the at least one brain;
   f) plotting, transposing, cross-referencing, and interrogating the brain maps and brain map data in the normalized brain mapping and reference system; and
   g) providing a means for simulating brain structures which may be combined with the brain maps and scanned images to create composite images on the display device so as to permit simulation of at least one of the group consisting of anatomical structures, physiological topography, and chemical topography of the brain of the patient.

* * * * *